US005882651A

United States Patent [19]
Murphy et al.

[11] Patent Number: 5,882,651
[45] Date of Patent: Mar. 16, 1999

[54] ATTENUATED RESPIRATORY SYNCYTIAL VIRUS VACCINE COMPOSITIONS

[75] Inventors: Brian R. Murphy; Robert M. Chanock, both of Bethesda; James E. Crowe, Jr.; Mark Connors, both of Chevy Chase, all of Md.; Kuo-Hom Lee Hsu, Fort Washington, Pa.; Alan R. Davis, Wayne, Pa.; Michael D. Lubeck, Glenmoore, Pa.; Bernard H. Selling, Bryn Mawr, Pa.

[73] Assignees: United States of America, Washington, D.C.; American Home Products Corporation, Parsippany, N.J.

[21] Appl. No.: 453,294

[22] Filed: May 30, 1995

Related U.S. Application Data

[60] Division of Ser. No. 327,263, Oct. 21, 1994, which is a continuation-in-part of Ser. No. 39,945, Apr. 9, 1993, abandoned, which is a continuation-in-part of Ser. No. 872,746, Apr. 21, 1992, abandoned.

[51] Int. Cl.$^6$ .......................... A61K 39/155; C12N 7/04; C12N 7/06; C12N 7/08
[52] U.S. Cl. .................................... 424/211.1; 424/204.1; 435/235.1; 435/236; 435/237; 435/238; 435/239
[58] Field of Search .............................. 424/204.1, 211.1, 424/235.1, 236, 237, 239, 238

[56] References Cited

U.S. PATENT DOCUMENTS

| 4,800,078 | 1/1989 | Prince et al. |
| 4,866,034 | 9/1989 | Ribi. |
| 5,250,298 | 10/1993 | Gelb. |

OTHER PUBLICATIONS

Beeler et al., J. Virology, 63, 2941–2950 (1989).
Edwards et al., J. Inf. Diseases, 163, 740–745 (1991).
Friedwald et al., J. Amer. Med. Assn., 204, 142–146 (May 20, 1968).
Kim et al., Pediatrics, 48, 745–755 (1971).
Murphy, Infect. Diseases, Clin. Prac., 2, 174–181 (1993).
Richardson et al., Archives of Virology, 54, 53–60 (1977).
Friedewald et al., "Low–Temperature–Grown RS Cirus in Adult Volunteers," *J. Amer. Med. Assoc.*, 204:690–694 (1968).
Gharpure et al., "Temperature–Sensitive Mutants of Respiratory Syncytial Virus," *J. Virol.*, 3:414–421 (1969).
Hodes et al., "Genetic Alteration in a Temperature Sensitive Mutant of Respiratory Syncytial Virus after Replication in vivo," *Proc. Soc. Exp. Biol. Med.*, 145:1158–1164 (1974).
McIntosh et al., "Attenuated Respiratory Syncytial Virus Vaccines in Asthmatic Children," *Pediatr. Res.*, 8:689–696 (1974).
Belshe et al., "Evaluation of Five Temperature–Sensitive Mutants of Respiratory Syncytial Virus in Primates: II. Genetic Analysis of Virus Recovered During Infection," *J. Med. Virol.*, 3:101–110 (1978).
Richardson et al., "Evaluation of Five Temperature–Sensitive Mutants of Respiratory Syncytial Virus in Primates: I. Viral Shedding, Immunologic Response and Associated Illness," *J. Med. Virol.*, 3:91–100 (1978).
Prince et al., "Respiratory Syncytial Virus Infection in Owl Monkeys: Viral Shedding, Immunological Response, and Associated Illness Caused by Wild–Type Virus and Two Temperature–Sensitive Mutants," *Infect. Immun.*, 26:1009–1013 (1979).
Murphy et al., "Production and Level of Genetic Stability of an Influenza A Virus Temperature–Sensitive Mutant Containing Two Genes with ts Mutations," *Infect. Immun.*, 37:235–242 (1982).
Wright et al., "Administration of a Highly Attenuated, Live Respiratory Syncytial Virus Vaccine to Adults and Children," *Infect. Immun.* 37:397–400 (1982).
Olmsted et al., "Expression of the F Glycoprotein of Respiratory Syncytial Virus by a Recombinant Vaccinia Virus: Comparison of the Individual Contributions of the F and G Glycoproteins to Host Immunity," *Proc. Natl. Acad. Sci.*, 83:7462–7466 (1986).
Walsh et al., "Immunization with Glycoprotein Subunits of Respiratory Syncytial Virus to Protect Cotton Rats Against Viral Infection," *J. Infect. Dis.*, 155:1198–1204 (1987).
Mufson et al., "Subgroup Characteristics of Respiratory Syncytial Virus Strains Recovered fromChildren with Two Consecutive Infections," *J. Clin. Microbiol.* 25:1535–1539 (1987).
Murphy et al., "Enhanced Pulmonary Histopathology is Observed in Cotton Rats Immunized with Formalin–Inactived Respiratory Syncytial Virus (RSV) or Purified F Glycoprotein and Challenged with RSV 3–6 Months after Immunization," *Vaccine*, 8:497–502 (1990).
Collins et al., "Evaluation in Chimpanzees of Vaccinia Virus Recombinants that Express the Surface Glycoproteins of Human Respiratory Syncytial Virus," *Vaccine*, 8:164–168 (1990).
Clements et al., "Evaluation of Bovine, Cold–Adapted Human and Wild–Type Human Parainfluenza Type 3 Viruses in Adult Volunteers and in Chimpanzees," *J. Clin. Microbiol.*, 29:1175–1182 (1991).

(List continued on next page.)

*Primary Examiner*—Anthony C. Caputa
*Attorney, Agent, or Firm*—Townsend and Townsend and Crew

[57] ABSTRACT

The present invention provides vaccine compositions of attenuated respiratory syncytial virus (RSV). More particularly, the attenuated virus may be a derivative of RSV which has been incompletely attenuated by cold-passage or introduction of mutations which produce virus having a temperature sensitive (ts) or cold adapted (ca) phenotype. The invention also provides methods for stimulating the immune system of an individual to induce protection against respiratory syncytial virus by administration of attenuated RSV. The invention also provides pure cultures of attenuated RS virus, wherein the virus has been more completely attenuated by the further derivatization of previously identified incompletely attenuated ts or cp mutants.

16 Claims, 1 Drawing Sheet

OTHER PUBLICATIONS

Edwards et al., "Safety and Immunogenicity of Live Attenuated Cold–Adapted Influenza B/Ann Arbor/1/86 Reassortant Virus Vaccine in Infants and Children," *J. Infect. Dis.* 163:740–745 (1991).

Crowe et al., "A Comparison in Chimpanzees of the Immunogenicity and Efficacy of Live Attenuated Respiratory Syncytial Virus (RSV) Temperature–Sensitive Mutant Vaccines and Vaccinia Virus Recombinants that Express the Surface Glycoproteins of RSV," *Vaccine* 11:1395–1404 (1993).

Pringle et al., "Immunogenicity and Pathogenicity of a Triple Temperature–Sensitive Modified Respiratory Syncytial Virus in Adult Volunteers," *Vaccine,* 11:473–478 (1993).

Maaspab et al., Vaccine 3:355–369 Dec. 1985.

Kalica et al., Arch. Ges. Virus for sch 41/3:248–58 (see abstract) 1973.

FIG. 1

Replication of RSV subgroup A mutants in the lungs of BALB/c mice correlates with replication in the nasopharynx of seronegative chimpanzees $y = 0.94254 + 0.79703x$   $R^2 = 0.630$

ATTENUATED RESPIRATORY SYNCYTIAL VIRUS VACCINE COMPOSITIONS

This is a divisional of application Ser. No. 08/327,263 filed on Oct. 21, 1994, which is a continuation-in-part of application Ser. No. 08/039,945, filed on Apr. 9, 1993, now abandoned, which is a continuation-in-part of Ser. No. 07/872,746, filed Apr. 21, 1992, now abandoned.

BACKGROUND OF THE INVENTION

Respiratory syncytial (RS) virus infection of humans ranges from asymptomatic to severe respiratory tract disease. In infants and children, RS virus (RSV) is regarded as one of the most important causes of lower respiratory tract disease in all geographic areas of the world. RS virus outranks all other microbial pathogens as a cause of pneumonia and bronchiolitis in infants under one year of age, and is a major cause of fatal respiratory tract disease in these infants. Virtually all children are infected by two years of age. Reinfection occurs with appreciable frequency in older children and young adults. (Chanock et al., in *Viral Infections of Humans*, 3rd ed., A. S. Evans, ed., Plenum Press, N.Y. (1989)). Although most healthy adults do not have serious disease due to RS virus infection, elderly patients and immunocompromised individuals are more likely to have severe and possibly life-threatening infections.

Treatment of RSV infection has been problematic. Small infants have diminished serum and secretory antibody responses to RSV antigens and thus suffer more severe infections, whereas cumulative immunity appears to protect older children and adults against more serious forms of the infection. One antiviral compound, ribavirin, has shown promise in the treatment of severely infected infants, although there is no indication that it shortens the duration of hospitalization or diminishes the infant's need for supportive therapy.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. Purified human immunoglobulin containing a high titer of neutralizing antibodies to RSV may prove useful in immunotherapeutic approaches for serious lower respiratory tract disease in infants and young children. Immune globulin preparations, however, suffer from several disadvantages, such as the possibility of transmitting blood-borne viruses and difficulty and expense in preparation and storage.

Despite an urgent need for an effective vaccine against RS virus, particularly for infants and young children, previous attempts to develop a safe and effective vaccine have met with failure. A formalin-inactivated virus vaccine tested in the mid-1960s failed to protect against RS virus infection or disease. Instead, disease was exacerbated during subsequent infection by RS virus. Kim et al., *Am. J. Epidemiol.* 89:422–434, Chin et al., *Am J. Epidemiol.* 89:449–463 (1969); Kapikian et al., *Am. J. Epidemiol.* 89:405–421 (1969).

To circumvent the problems attendant with the inactivated vaccines and the possible alteration of neutralization epitopes, efforts were directed to developing attenuated RS mutants. Friedewald et al., *J. Amer. Med. Assoc.* 204:690–694 (1968) reported the production of a low-temperature passaged mutant of RS virus which appeared to possess sufficient attenuation to be a candidate vaccine. This mutant exhibited a slight increased efficiency of growth at 26° C. compared to its wild-type parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the mutant retained a low level virulence for the upper respiratory tract of seronegative infants. This RSV mutant had been passaged in bovine kidney cell culture at low temperature (26° C.) and as a consequence it acquired host range attenuating mutations. The acquisition of these mutations allowed the mutant to replicate efficiently in bovine tissue, whereas these same mutations restricted growth of the mutant in the human respiratory tract compared to its RSV strain A2 parent.

Similarly, Gharpure et al., *J. Virol.* 3:414–421 (1969) reported the isolation of temperature sensitive (ts) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected, although virus exhibiting a partial or complete loss of temperature sensitivity represented a small proportion of virus recoverable from vaccinees, and was not associated with signs of disease other than mild rhinitis.

The aforementioned studies thus revealed that among the cold-passaged and temperature sensitive strains some were underattenuated and caused mild symptoms of disease in some vaccinees, particularly seronegative infants, while others were overattenuated and failed to replicate sufficiently to elicit protective immune responses. (Wright et al., *Infect. Immun.* 37:397–400 (1982)). The genetic instability that allowed candidate vaccine mutants to lose their temperature-sensitive phenotype was also a disconcerting discovery. See generally, Hodes et al., *Proc. Soc. Exp. Biol. Med.* 145:1158–1164 (1974), McIntosh et al. *Pediatr. Res.* 8:689–696 (1974), and Belshe et al., *J. Med. Virol.* 3:101–110 (1978).

Abandoning the attenuated RS virus vaccine approach, investigators tested potential subunit vaccine candidates using purified RS virus envelope glycoproteins from lysates of infected cells. The glycoproteins induced resistance to RS virus infection in the lungs of cotton rats, Walsh et al., *J. Infect. Dis.* 155:1198–1204 (1987), but the antibodies induced had very weak neutralizing activity and immunization of rodents with purified subunit vaccine led to disease potentiation (Murphy et al., *Vaccine* 8:497–502 (1990)).

Vaccinia virus recombinant-based vaccines which express the F or G envelope glycoprotein have also been explored. These recombinants express RSV glycoproteins which are indistinguishable from the authentic viral counterpart, and small rodents infected intradermally with the vaccinia-RSV F and G recombinant viruses developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. Olmsted et al., *Proc. Natl. Acad. Sci. USA* 83:7462–7466 (1986). However, immunization of chimpanzees with vaccinia F and vaccinia G recombinant provided almost no protection against RSV challenge in the upper respiratory tract (Collins et al., *Vaccine* 8:164–168 (1990)) and inconsistent protection in the lower respiratory tract (Crowe et al., *Vaccine* 11:1395–1404 (1993). This led to the conclusion that this approach was not likely to yield a successful vaccine.

While investigators examined several different approaches to producing an effective and safe RS vaccine over the years, RS virus has remained the most common cause of severe viral lower respiratory tract disease in infants and children. Consequently, an urgent need remains for a safe vaccine that is able to prevent the serious illness in this population that often requires hospitalization, and to prevent disease in other individuals. Quite surprisingly, the present invention fulfills these and other related needs.

SUMMARY OF THE INVENTION

The present invention provides vaccine compositions of attenuated respiratory syncytial virus. The attenuated virus is provided in an amount sufficient to induce an immune response in a human host, in conjunction with a physiologically acceptable carrier and may optionally include an adjuvant to enhance the immune response of the host. The invention contemplates several distinct antigenic subgroups of attenuated RS virus which are derived from incompletely attenuated RS virus and which possess properties heretofore not exhibited by attenuated RS viruses previously reported in the literature. In one embodiment thereof, the attenuated virus of the invention comprises host range restricted RS virus (i.e. virus possessing mutations that restrict replication in the lung of the host) incompletely attenuated by cold-passage (cpRSV) into which at least one or more additional mutations are introduced to produce a virus and its progeny having a temperature sensitive (ts) phenotype, which are hereinafter designated cptsRSV. In another embodiment, host-range restricted RS virus incompletely attenuated by cold-passage (cpRSV) is cold adapted (ca) by passage at increasingly reduced temperatures to introduce additional growth restriction mutations. In yet another embodiment, incompletely atttenuated RSV ts mutants, such as RSV ts-4 and ts-1,NG1 are further attenuated by introduction of additional mutations. The attenuated derivatives of the ts or cp strains are produced in several ways, but preferably by introduction of additional temperature sensitive-mutations by chemical mutagenesis, by further passage in culture at attenuating temperatures of 20°–24° C., or by introduction of small plaque (sp) mutations and selection of derivatives which are more restricted in replication than the incompletely attenuated parental mutant strain. The attenuated virus of the invention belongs to either antigenic subgroup A or B, and virus from both subgroups may conveniently be combined in vaccine formulations for more comprehensive coverage against prevalent RSV infections. The vaccine will typically be formulated in a dose of from about $10^3$ to $10^6$ plaque-forming units (PFU) or more for maximal efficacy.

In other embodiments, the invention provides methods for stimulating the immune system of an individual to induce protection against respiratory syncytial virus. These methods comprise administering to the individual an immunologically sufficient amount of RSV which has been attenuated by introducing mutations that specify the ts, ca, and/or sp phenotype into RSV which was originally incompletely attenuated by ts mutation(s) or by passage at cold temperature, e.g., 26° C. In view of the potentially serious consequences of RSV infection in neonates, seronegative and seropositive infants and young children, and the elderly, these individuals will typically benefit most from immunization according to the present methods. In this regard, seronegative individuals are those who exhibit no evidence of previous infection with a subgroup A or B RS virus, while seropositive individuals can be classified as those with no previous infection with RSV, but with RSV antibodies that have been acquired passively from the mother, as well as those individuals who have RSV antibodies due to past infection with RSV. A titer of neutralizing antibody of equal to or greater than 1:20 is considered a seropositive condition. In most instances the attenuated RS virus is administered to the respiratory tract of the individual, preferably intranasally by aerosol or droplet application. The attenuated RS viruses of the invention have been deposited under the terms of the Budapest Treaty with the American Type Culture Collection (ATCC) of 12301 Parklawn Drive, Rockville, Md. 20852, U.S.A., and were granted the accession numbers as follows:

| Virus Name | ATCC Designation |
| --- | --- |
| RSV A2 cpts - 248 | VR 2450 |
| RSV A2 cpts - 530/1009 | VR 2451 |
| RSV A2 cpts - 530 | VR 2452 |
| RSV A2 cpts - 248/955 | VR 2453 |
| RSV A2 cpts - 248/404 | VR 2454 |
| RSV A2 cpts - 530/1030 | VR 2455 |

In yet other embodiments, the invention provides pure cultures of attenuated RS virus, wherein the virus has been more completely attenuated by the further derivatization of previously identified ts or cp mutants. The attenuated virus is capable of eliciting a protective immune response in an infected human host yet is sufficiently attenuated so as to not cause unacceptable symptoms of severe respiratory disease in the immunized host. The attenuated virus may be present in a cell culture supernatant, isolated from the culture, or partially-or completely purified. The virus may also be lyophilized, and can be combined with a variety of other components for storage or delivery to a host, as desired.

DESCRIPTION OF THE DRAWINGS

FIG. 1 is a graph demonstrating the substantially complete correlation between the replication of a series of subgroup A respiratory syncytial viruses in the lungs of mice with their replication in the chimpanzee.

DESCRIPTION OF THE SPECIFIC EMBODIMENTS

The present invention provides RS virus suitable for vaccine use in humans. The RS virus described herein is produced by introducing additional mutations into incompletely attenuated strains of ts or cp RS virus. The mutations are introduced into the strains during virus growth in cell cultures to which a chemical mutagen has been added, by selection of virus that has been subjected to passage at suboptimal temperature in order to introduce growth restriction mutations, or by selection of mutagenized virus that produces small plaques in cell culture.

Thus, the vaccine of the invention comprises the attenuated RV virus and a physiologically acceptable carrier. The vaccine is administered in an immunogenically sufficient amount to an individual in need of immunological protection against RS virus, such as, e.g., an infant, child, the elderly, or adult candidates for immunosuppressive therapies. The vaccine elicits the production of an immune response that is protective against serious lower respiratory tract disease, such as pneumonia and bronchiolitis when the individual is subsequently infected with wild-type RS virus. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, i.e., against heterologous strains of another subgroup, it is preferred to vaccinate individuals with attenuated RS virus from at least one predominant strain of both subgroups A and B.

The attenuated virus which is a component of the vaccine is in an isolated and typically purified form. By isolated is meant to refer to attenuated modified RS virus which is in other than the native environment of wild-type virus, such as the nasopharynx of an infected individual. More generally, isolated is meant to include the attenuated virus as a heterologous component of a cell culture or other system. For example, attenuated RS virus of the invention may be produced by an infected cell culture, separated from the cell culture and added to a stabilizer which contains other non-naturally occurring RS viruses, such as those which are selected to be attenuated by means of resistance to neutralizing monoclonal antibodies to the F-protein, as described in co-filed U.S. patent application attorney docket 15280-11-2, the disclosure of which is expressly incorporated herein by reference.

The attenuated RS virus of the present invention exhibits a very substantial diminition of virulence when compared to wild-type virus that is circulating naturally in humans. The attenuated virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation may be determined by, for example, quantifying the amount of virus present in the respiratory tract of an immunized host and comparing the amount to that produced by wild-type RS virus or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, Belshe et al., *J. Med. Virology* 1:157–162 (1977), Friedewald et al., *J. Amer. Med. Assoc.* 204:690–694 (1968); Gharpure et al., *J. Virol.* 3:414–421 (1969); and Wright et al., *Arch. Ges. Virusforsch.* 41:238–247 (1973). The virus can conveniently be measured in the nasopharynx of host animals, such as chimpanzees.

To produce a satisfactorily attenuated derivative virus of the present invention, mutations are introduced into a parental viral strain which has been incompletely or partially attenuated, such as the ts-1 or ts-4 mutant, or cpRSV. For virus of subgroup A, the incompletely attenuated parental virus is preferably ts-1 or ts-1 NG-1 or cpRSV, which are mutants of the A2 strain of subgroup A, or derivatives or subclones thereof.

Partially attenuated mutants of the subgroup B virus can be produced by biologically cloning wild-type subgroup B virus in an acceptable cell substrate and developing cold-passaged mutants thereof, subjecting the virus to chemical mutagenesis to produce ts mutants, or selecting small plaque mutants thereof. For virus of subgroup B, the incompletely attenuated parental virus is preferably cp 52/2B5, which is a mutant of the B 1 strain of subgroup B. The various selection techniques may also be combined to produce the partially attenuated mutants of subgroup A or B which are useful for further derivatization as described herein.

Once the desired partially attenuated parental strain(s) is/are selected, further attenuation sufficient to produce a vaccine acceptable for use in humans according to the present invention may be accomplished in several ways as described herein.

According to the present invention the cp mutant can be further mutagenized in several ways. In one embodiment the procedure involves subjecting the partially attenuated virus to passage in cell culture at progressively lower, attenuating temperatures. For example, whereas wild-type virus is typically cultivated at about 34°–37° C., the partially attenuated mutants are produced by passage in cell cultures (e.g., primary bovine kidney cells) at suboptimal temperatures, e.g., 20°–26° C. These mutants have slight but definite evidence of cold adaptation (ca), i.e., increased efficiency of growth at 26° C. compared to its wild-type parental virus, but typically are not ts. Thus, in one method of the present invention the cp mutant or other partially attenuated strain, e.g., ts-1 or sp, is adapted to efficient growth at a lower temperature by passage in MRC-5 or Vero cells, down to a temperature of about 20°–24° C., preferably 20°–22° C. This selection of mutant RS virus during cold-passage substantially eliminates any residual virulence in the derivative strains as compared to the partially attenuated parent.

In another embodiment of the invention the incompletely attenuated strains are subjected to chemical mutagenesis to introduce ts mutations or, in the case of viruses which are already ts, additional ts mutations sufficient to confer increased stability of the ts phenotype on the attenuated derivative. Means for the introduction of ts mutations into RS virus include replication of the virus in the presence of a mutagen such as 5-fluorouridine or 5-fluorouracil in a concentration of about $10^{-3}$ to $10^{-5}$M, preferably about $10^{-4}$M, or exposure of virus to nitrosoguanidine at a concentration of about 100 $\mu$g/ml, according to the general procedure described in, e.g., Gharpure et al., *J. Virol.* 3:414–421 (1969) and Richardson et al., *J. Med. Virol.* 3:91–100 (1978). Other chemical mutagens can also be used. Attenuation can result from a ts mutation in almost any RS virus gene. The level of temperature sensitivity of the replication of the attenuated RS virus of the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RS virus correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35° to 37° C. should be fully attenuated in humans. Thus, the attenuated RS virus of the invention which is temperature-sensitive will have a shutoff temperature in the range of about 35° to 39° C., and preferably from 35° to 38° C. The addition of the temperature sensitive property to a partially attenuated strain produces completely attenuated virus useful in the vaccine compositions of the present invention.

In addition to the criteria of viability, attenuation and immunogenicity, the properties of the derivative which are selected must also be as stable as possible so that the desired attributes are maintained. Genetic instability of the ts phenotype following replication in vivo has been the rule for ts viruses (Murphy et al., Infect. and Immun. 37:235–242 (1982)). Ideally, then, the virus which is useful in the vaccines of the present invention must maintain its viability, its property of attenuation, its ability to replicate in the immunized host (albeit at lower levels), and its ability to effectively elicit the production of an immune response in the vaccinee that is sufficient to confer protection against serious disease caused by subsequent infection by wild-type virus. Clearly, the heretofore known and reported RS virus mutants do not meet all of these criteria. Indeed, contrary to expectations based on the results reported for known attenuated RS viruses, some of the viruses of the invention, which have a minimun of two to three distinct mutations, are not only viable and more attenuated then previous mutants, but are more stable genetically in vivo than those previously studied mutants, retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Propagation of the attenuated virus of the invention may be in a number of cell lines which allow for RS virus growth. RS virus grows in a variety of human and animal cells. Preferred cell lines for propagation of attenuated RS virus for vaccine use include DBS-FRhL-2, MRC-5, and Vero cells. Highest virus yields are usually achieved with heteroploid cell lines such as Vero cells. Cells are typically inoculated with virus at a multiplicity of infection ranging from about 0.001 to 1.0 or more, and are cultivated under conditions permissive for replication of the virus, e.g., at about 30°–37° C. and for about 3–5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

RS virus which has been attenuated as described herein can be tested in in vitro and in vivo models to confirm adequate attenuation, genetic stability, and immunogencity for vaccine use. In in vitro assays, the modified virus is tested for temperature sensitivity of virus replication, i.e. ts phenotype, and for the small plaque phenotype. Modified viruses are further tested in animal models of RS infection. A variety of animal models have been described and are summarized in Meignier et al., eds., Animal Models of Respiratory Syncytial Virus Infection, Merieux Foundation Publication, (1991), which is incorporated herein by reference. A cotton rat model of RS infection is described in U.S. Pat. No. 4,800,078 and Prince et al., Virus Res. 3:193–206 (1985), which are incorporated herein by reference, and is believed to be predictive of attenuation and efficacy in humans. A primate model of RS infection using the chimpanzee is predictive of attenuation and efficacy in humans, and is described in detail in Richardson et al., J. Med. Virol. 3:91–100 (1978); Wright et al., Infect. Immun., 37:397–400 (1982); Crowe et al., Vaccine 11:1395–1404 (1993), which are incorporated herein by reference.

The interrelatedness of data derived from rodents and chimpanzees relating to the level of attenuation of RSV candidates can be demonstrated by reference to FIG. 1, which is a graph correlating the replication of a spectrum of respiratory syncytial subgroup A viruses in the lungs of mice with their replication in chimpanzees. The replication is substantially identical, allowing the mouse to serve as a model in which to initially characterize the level of attenuation of the vaccine RSV candidate. The mouse and cotton rat model are especially useful in those instances in which candidate RS viruses display inadequate growth in chimpanzees. The RSV subgroup B viruses are an example of the RS viruses which grow poorly in chimpanzees.

Moreover, the therapeutic effect of RSV neutralizing antibodies in infected cotton rats has been shown to be highly relevant to subsequent experience with immunotherapy of monkeys and humans infected with RSV. Indeed, the cotton rat appears to be a reliable experimental surrogate for the response of infected monkeys, chimpanzees and humans to immunotherapy with RSV neutralizing antibodies. For example, the amount of RSV neutralizing antibodies associated with a therapeutic effect in cotton rats as measured by the level of such antibodies in the serum of treated animals (i.e., serum RSV neutralization titer of 1:302 to 1:518) is in the same range as that demonstrated for monkeys (i.e., titer of 1:539) or human infants or small children (i.e., 1:877). A therapeutic effect in cotton rats was manifest by a one hundred fold or greater reduction in virus titer in the lung (Prince et al., J. Virol. 61:1851–1854) while in monkeys a therapeutic effect was observed to be a 50-fold reduction in pulmonary virus titer. (Hemming et al., J. Infect. Dis. 152:1083–1087 (1985)). Finally, a therapeutic effect in infants and young children who were hospitalized for serious RSV bronchiolitis or pneumonia was manifest by a significant increase in oxygenation in the treated group and a significant decrease in amount of RSV recoverable from the upper respiratory tract of treated patients. (Hemming et al., Antimicrob. Agents Chemother. 31:1882–1886 (1987)). Therefore, based on these studies, it would appear that the cotton rat constitutes a relevant model for predicting the success of an RSV vaccine in infants and small children. Other rodents, including mice, should also be similarly useful because these animals are permissive for RSV replication and have a core temperature more like that of humans (Wight et al., J. Infect. Dis. 122:501–512 (1970) and Anderson et al., J. Gen. Virol. 71:(1990)).

For vaccine use, the attenuated virus of the invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, Mg$^{++}$and HEPES, with or without adjuvant, as further described below.

Thus RS virus vaccines of the invention contain as an active ingredient an immunogenically effective amount of an attenuated RS virus as described herein. The attenuated virus may be introduced into a host, particularly humans, with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Upon inoculation with an attenuated RS virus composition as described herein, via aerosol, droplet, coarse spray, oral, topical or other route, most preferably suitable for intranasal delivery, the immune system of the host responds to the vaccine by producing antibodies, both secretory and serum, specific for RS virus proteins. As a result of the vaccination the host becomes at least partially or completely immune to RS virus infection, or resistant to developing moderate or severe RS viral infection, particularly of the lower respiratory tract.

The vaccine compositions containing the attenuated RS virus of the invention are administered to a person susceptible to or otherwise at risk of RS virus infection to enhance the individual's own immune response capabilities. Such an amount is defined to be a "immunogenically effective dose." In this use, the precise amounts again depend on the patient's state of health and weight, the mode of administration, the nature of the formulation, etc., but generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated RS virus of the invention sufficient to effectively protect the patient against serious or life-threatening RS virus infection.

The attenuated RS virus of the invention of one particular RS subgroup or strain can be combined with attenuated viruses of the other subgroup or strains to achieve protection against multiple RS viruses. Typically the different modified viruses will be in admixture and administered simultaneously, but may also be administered separately. Due to the phenomenon of cross-protection among certain strains of RS virus, immunization with one strain may protect against several different strains of the same or different subgroup.

In some instances it may be desirable to combine the attenuated RS virus vaccines of the invention with vaccines which induce protective responses to other agents, particularly other childhood viruses. For example, the attenuated virus vaccine of the present invention can be administered simultaneously (typically separately) or sequentially with parainfluenza virus vaccine, such as described in Clements et al., *J. Clin Microbiol.* 29:1175–1182 (1991), which is incorporated herein by reference.

Single or multiple administrations of the vaccine compositions of the invention can be carried out. In neonates and infants, multiple administration may be required to elicit sufficient levels of immunity. Administration should begin within the first month of life, and continue at intervals throughout childhood, such as at two months, six months, one year and two years, as necessary to maintain sufficient levels of protection against native (wild-type) RS virus infection. Similarly, adults who are particularly susceptible to repeated or serious RS virus infection, such as, for example, health care workers, day care workers, family members of young children, elderly, individuals with compromised cardiopulmonary function, etc. may require multiple immunizations to establish and/or maintain protective imune responses. Levels of induced immunity can be monitored by measuring amounts of neutralizing secretory and serum antibodies, and dosages adjusted or vaccinations repeated as necessary to maintain desired levels of protection.

The following examples are provided by way of illustration, not limitation.

EXAMPLE I

Isolation and Characterization of Mutagenized Derivatives of Cold-passaged RSV

This Example describes the chemical mutagenesis of incompletely attenuated host range-restricted cpRSV to produce derivative ts and sp strains which are more highly attenuated and thus are preferred for use in RSV vaccine preparations.

A parent stock of cold-passaged RSV (cpRSV) was prepared. Flow Laboratories Lot 3131 virus, the cpRSV parent virus that is incompletely attenuated in humans, was passaged twice in MRC-5 cells at 25° C., terminally diluted twice in MRC-5 cells at 25° C., then passaged three times in MRC-5 to create a cpRSV suspension for mutagenesis.

The cpRSV was mutagenized by growing the parent stock in MRC-5 cells at 32° C. in the presence of 5-fluorouracil in the medium at a concentration of $4\times10^{-4}$M. This concentration was demonstrated to be optimal in preliminary studies, as evidenced by a 100-fold decrease in virus titer on day 5 of growth in cell culture, compared to medium without 5-fluorouracil. The mutagenized stock was then analyzed by plaque assay on Vero cells that were maintained under an agar overlay, and after an appropriate interval of incubation, plaques were stained with neutral red dye. 854 plaques were picked and the progeny of each plaque were separately amplified by growth on fresh monolayers of Vero cells. The contents of each of the tissue cultures inoculated with the progeny of a single plaque of cpRSV-mutagenized virus were separately harvested when cytopathic effects on the Vero cells appeared maximal. Progeny virus that exhibited the temperature-sensitive (ts) or small-plaque (sp) phenotype was sought by titering these plaque pools on HEp-2 cells at 32° C. and 38° C. Any virus exhibiting a sp phenotype (plaque size that was reduced by 50% or more compared to parental virus at 32° C.) or a ts phenotype (100-fold or greater reduction in titer at restrictive temperature [37° to 40° C.] compared to 32° C.) was evaluated further. These strains were biologically cloned by serial plaque-purification on Vero cells three times, then amplified on Vero cells. The cloned strains were tired at 32°, 37°, 38°, 39° and 40° C. (in an efficiency of plaque formation (EOP) assay) to confirm their sp and ts phenotypes. Because titers of some cloned strains were relatively low even at the permissive temperature (32°), these viruses were passaged once in HEp-2 cells to create virus suspensions for in vitro analysis. The phenotypes of the progeny of the mutagenized cpRSV are presented on Table 1.

cpRSV progeny that were among the most ts, namely ts 248 and ts 530. Nude mice were selected because they are immunocompromised due to congenital absence of functional T-cells, and a virus can replicate for a much longer

TABLE 1

The efficiency of plaque formation of nine derivatives of cold-passaged RSV (cpts or cpsp mutants) in HEp-2 cells at permissive and restrictive temperatures

| Virus | The titer of virus ($log_{10}$pfu/ml) at the indicated temperature (°C.) | | | | | Shut-off temperature (°C.)[1] | Small-plaques at 32 C. |
|---|---|---|---|---|---|---|---|
|  | 32 | 37 | 38 | 39 | 40 |  |  |
| A2 wild-type | 4.5 | 4.4 | 4.5 | 3.8 | 3.8 | >40 | no |
| cp-RSV | 6.0 | 5.8 | 5.8 | 6.2 | 5.4 | >40 | no |
| ts-1 | 5.7 | 4.5 | 2.7 | 2.4 | 1.7* | 38 | no |
| cpsp-143 | 4.2* | 4.1* | 3.8* | 3.9* | 3.8* | >40 | yes |
| cpts-368 | 6.7 | 6.3 | 6.1* | 5.8** | 2.0** | 40 | no |
| cpts-274 | 7.3 | 7.1 | 6.6 | 5.8* | 1.0** | 40 | no |
| cpts-347 | 6.2 | 6.1 | 5.7* | 5.5** | <0.7 | 40 | no |
| cpts-142 | 5.7 | 5.1 | 4.5* | 3.7** | <0.7 | 39 | no |
| cpts-299 | 6.2 | 5.5 | 5.1* | 2.0** | <0.7 | 39 | no |
| cpts-475 | 5.4 | 4.8* | 4.2** | <0.7 | <0.7 | 39 | no |
| cpts-530 | 5.5 | 4.8* | 4.5* | <0.7 | <0.7 | 39 | no |
| cpts 248 | 6.3 | 5.3** | <0.7 | <0.7 | <0.7 | 38 | no |

[1]Shut-off temperature is defined as the lowest restrictive temperature at which a 100-fold or greater reduction of plaque fiter is observed (bold figures in table).
*Small plaque phenotype (<50% wild-type plaque size)
**Pinpoint plaque phenotype (<10% wild-type plaque size)

One of the mutant progeny had the small plaque phenotype, RSV cpsp-143 (sp refers to the small plaque (sp) phenotype), and the remaining mutant progeny had the ts phenotype. The RSV cpts mutants exhibit a variation in ability to produce plaques in monolayer cultures in vitro over the temperature range 37° C. to 40° C., with cpts 368 retaining the ability to produce plaques at 40° C., whereas the most temperature-sensitive (ts) virus, cpts 248, failed to produce plaques at 38° C. Thus, several of the mutagenized cpRSV progeny exhibit a marked difference from their cpRSV parent virus with respect to temperature-sensitivity of plaque formation.

Replication and Genetic Stability Studies In Mice

The level of replication of the cpRSV derived mutants in the upper and lower respiratory tracts of BALB/c mice was studied next (Table 2). It was found that cpts 530 and cpts 248, two of the mutants exhibiting the greatest temperature sensitivity (see Table 1), were about 7- to 12-fold restricted in replication in the nasal turbinates of the mice (Table 2). However, none of the viruses was restricted in replication in the lungs compared to the cpRSV parent virus. This greater restriction of replication in the nasal turbinates than in the lungs is not characteristic of ts mutants, which generally are more restricted in replication in the warmer lower respiratory tract (Richman and Murphy, Rev. Infect. Dis. 1:413–433 (1979). The virus produced in the lungs and nasal turbinates retained the ts character of the input virus (data not presented). The present findings suggested that the combination of the ts mutations on the background of the mutations of the cp parent virus has resulted in cpRSV ts progeny with a higher level of stability of the ts phenotype after replication in vivo than had been seen with previously studied ts mutants.

To further explore the level of genetic stability of the ts phenotype of the cpRSV derived mutants, the efficiency of plaque formation of virus present in the lungs and nasal turbinates of nude mice was studied for two mutagenized period of time in these hosts. This longer period of replication favors the emergence of virus mutants with altered phenotype. The virus present on day 12 (NOTE: in normal mice, virus is no longer detectable at this time) was characterized and found to retain an unaltered ts phenotype (Table 3). As expected, the ts-1 mutant included in the test as a positive control exhibited an unstable ts phenotype in vivo. Thus, contrary to previous evaluation of ts mutant viruses in rodents, the results show that a high level of stability of the ts phenotype of the cpRSV derived mutants following prolonged replication in rodents was achieved, which represents a significant and heretofore unattained very desirable property in the viruses of the invention.

TABLE 2

Replication of cpts - RSV mutants in BALB/c mice[1]
Virus titer at 32° C. (mean $log_{10}$pfu/g tissue from the tissues of eight animals ± standard error)

| Animals infected with | Shutoff temperature of virus (°C.) | Day 4 | | Day 5 | |
|---|---|---|---|---|---|
|  |  | Nasal Turbinates | Lungs | Nasal turbinates | Lungs |
| A2 wild-type | >40 | 5.0 ± 0.16 | 5.8 ± 0.20 | 5.0 ± 0.11 | 5.8 ± 0.19 |
| cp-RSV | >40 | 4.7 ± 0.07 | 5.3 ± 0.18 | 4.8 ± 0.16 | 5.3 ± 0.21 |
| ts-1 | 38 | 4.0 ± 0.19 | 4.7 ± 0.21 | 3.8 ± 0.33 | 4.9 ± 0.13 |
| cpsp-143 | >40 | 4.5 ± 0.14 | 4.1 ± 0.37 | 4.4 ± 0.39 | 4.6 ± 0.39 |
| cpts-368 | 40 | 4.8 ± 0.15 | 5.1 ± 0.35 | 4.7 ± 0.08 | 5.4 ± 0.23 |
| cpts-274 | 40 | 4.2 ± 0.19 | 5.0 ± 0.15 | 4.2 ± 0.11 | 5.1 ± 0.55 |
| cpts-347 | 40 | 4.4 ± 0.32 | 4.9 ± 0.40 | 4.5 ± 0.33 | 5.2 ± 0.35 |
| cpts-142 | 39 | 4.1 ± 0.34 | 5.0 ± 0.19 | 4.3 ± 0.24 | 5.8 ± 0.40 |
| cpts-299 | 39 | 3.9 ± 0.11 | 5.2 ± 0.15 | 3.9 ± 0.32 | 5.0 ± 0.29 |
| cpts-475 | 39 | 4.0 ± 0.18 | 5.3 ± 0.25 | 4.1 ± 0.23 | 4.9 ± 0.42 |
| cpts-530 | 39 | 3.9 ± 0.18 | 5.3 ± 0.15 | 3.9 ± 0.14 | 5.3 ± 0.19 |
| cpts-248 | 38 | 3.9 ± 0.33 | 5.1 ± 0.29 | 4.2 ± 0.13 | 5.5 ± 0.35 |

[1]Mice were administered $10^{6.3}$ p.f.u. intranasally in a 0.1 ml inoculum on day 0, then sacrificed on day 4 or 5.

TABLE 3

The genetic stability of RSV cpts-248 and cpts-530 following prolonged replication in nude nice Efficiency of plaque formation at indicated temperature of virus present in nasal turrbinates (n.t.) or lungs of nude mice sacrificed 12 days after virus administration[1]

| Animals infected with | Tissue harvest or input virus tested | Number of animals | 32° C. | | 37° C. | | | 38° C. | | | 40° C. | | |
|---|---|---|---|---|---|---|---|---|---|---|---|---|---|
| | | | % animals with virus detectable | Mean titer ($\log_{10}$pfu per gram tissue or ml inoculum) | % animals with virus detectable | % animals with virus with altered ts phenotype | Mean titer ($\log_{10}$pfu per gram tissue or ml inoculum) | % animals with virus detectable | % animals with virus with altered ts phenotype | Mean titer ($\log_{10}$pfu per gram tissue or ml inoculum) | % animals with virus detectable | % animals with virus with altered ts phenotype | Mean titer ($\log_{10}$pfu per gram tissue or ml inoculum) |
| cpts-248 | n.t. | 19 | 100 | 3.8 ± 0.34 | 0 | 0 | <2.0 | 0 | 0 | <2.0 | 0 | 0 | <2.0 |
| " | lungs | " | 90 | 2.0 ± 0.29 | 0 | 0 | <1.7 | 0 | 0 | <1.7 | 0 | 0 | <1.7 |
| cpts-530 | n.t. | 20 | 100 | 3.0 ± 0.26 | 0 | 0 | <2.0 | 0 | 0 | <2.0 | 0 | 0 | <2.0 |
| " | lungs | " | 100 | 2.4 ± 0.29 | 0 | 0 | <1.7 | 0 | 0 | <1.7 | 0 | 0 | <1.7 |
| ts-1 | n.t. | 19 | 100 | 3.7 ± 0.23 | 74 | 74 | 2.7 ± 0.57 | 63 | 63 | 2.4 ± 0.36 | 10 | 10 | 2.0 ± 0.13 |
| " | tungs | " | 100 | 2.5 ± 0.30 | 74 | 74 | 1.8 ± 0.21 | 3.5 | 32 | 1.8 ± 0.15 | 0 | 0 | <1.7 |
| Efficiency of plaque formation of input | cpts-248 | — | — | 4.9 | — | | <0.7 | — | | <0.7 | — | | <0.7 |
| | cpts-530 | — | — | 5.5 | — | | 3.7* | — | | <0.7 | — | | <0.7 |
| | ts-t | — | — | 6.1 | — | | 3.3 | — | | 2.7 | — | | <0.7 |

[1]Plaque titers shown represent the mean $\log_{10}$pfu/gram tissue of 19 or 20 samples ± standard error
[2]Each animal received $10^{6.3}$ p.f.u. intranasally in a 0.1 ml inoculum of the indicated virus on day 0.
*Small plaque phenotype only.

In Chimpanzees

The level of attenuation of the cpRSV ts progeny was next evaluated in the seronegative chimpanzee, a host most closely related to humans. Trials in chimpanzees or owl monkeys are conducted according to the general protocol of Richardson et al., *J. Med. Virol.* 3:91–100 (1979); Crowe et al., *Vaccine* 11:1395–1404 (1993), which are incorporated herein by reference. One ml of suspension containing approximately $10^4$ plaque-forming units (PFU) of mutagenized, attenuated virus is given intranasally to each animal. An alternate procedure is to inoculate the RSV into both the upper and lower respiratory tract at a dose of $10^4$ PFU delivered to each site. Chimpanzees are sampled daily for 10 days, then every 3–4 days through day 20. The lower respiratory tract of chimpanzees can be sampled by tracheal lavage according to the protocol of Snyder et al., *J. Infec. Dis.* 154:370–371 (1986) and Crowe et al., *Vaccine* 11:1395–1404 (1993). Some animals are challenged 4 to 6 weeks later with the wild-type virus. Animals are evaluated for signs of respiratory disease each day that nasopharyngeal specimens are taken. Rhinorrhea is scored from 0 to 4+, with 2+ or greater being considered as evidence of significant upper respiratory disease.

Virus is isolated from nasal and throat swab specimens and tracheal lavage fluids by inoculation into RSV-sensitive HEp-2 cells as described above. Quantities of virus can also be determined directly by the plaque technique using HEp-2 cells as described in Schnitzer et al., *J. Virol.* 17:431–438 (1976), which is incorporated herein by reference. Specimens of serum are collected before administration of virus and at 3 to 4 weeks post-inoculation for determination of RSV neutralizing antibodies as described in Mills et al., *J. Immunol.* 107:123–130 (1970), which is incorporated herein by reference.

The most ts and attenuated of the cpRSV progeny (cpts 248) was studied and compared to wild-type RSV and the cpRSV parent virus (Table 4). Replication of the cpRSV parent virus was slightly reduced in the nasopharynx compared to wild-type, there was a reduction in the amount of rhinorrhea compared to wild-type virus, and there was an approximate 600-fold reduction in virus replication in the lower respiratory tract compared to wild-type. Clearly, the cp virus was significantly restricted in replication in the lower respiratory tract of chimpanzees, a very desirable property not previously identified from prior evaluations of cpRSV in animals or humans. More significantly, the cpts 248 virus was 10-fold restricted in replication in the nasopharynx compared to wild-type, and this restriction was associated with a marked reduction of rhinorrhea. These findings indicated that the cpRSV derived mutant possesses two highly desirable properties for a live RSV vaccine, namely, evidence of attenuation in both the upper and the lower respiratory tracts of highly susceptible seronegative chimpanzees. The level of genetic stability of the virus present in the respiratory tract of chimpanzees immunized with cpts-248 was evaluated next (Table 5). The virus present in the respiratory tract secretions retained the ts phenotype, and this was seen even with the virus from chimpanzee No. 3 on day 8 that was reduced 100-fold in titer at 40° C. and exhibited the small plaque phenotype at 40° C., indicating that its replication was still temperature-sensitive. This represents the most genetically stable ts mutant identified prior to the time of this test. The increased stability of the ts phenotype of the cpts 248 and cpts 530 viruses reflects an effect of the cp mutations on the genetic stability of the mutations that contribute to the ts phenotype in vivo. Thus, the ts mutations in the context of the mutations already present in the cp3131 parent virus appear to be more stable than would be expected in their absence. This important property has not been previously observed or reported. Infection of chimpanzees with the cpts 248 induced a high titer of serum neutralizing antibodies, as well as antibodies to the F and G glycoproteins (Table 6). Significantly, immunization with cpts 248 protected the animals from wild-type RSV challenge (Table 7), indicating that this mutant functions as an effective vaccine virus in a host that is closely related to humans.

These above-presented findings indicate that the cpts 248 virus has many properties desirable for a live RSV vaccine, including: 1) attenuation for the upper and lower respiratory tract; 2) increased genetic stability after replication in vivo, even after prolonged replication in immunosuppressed animals; 3) satisfactory immunogenicity; and 4) significant protective efficacy against challenge with wild-type RSV. The cpts 530 virus shares with cpts 248 similar temperature sensitivity of plaque formation, a similar degree of restriction of replication in the nasal turbinates of mice, and a high level of genetic stability in immunodeficient nude mice, whereby it also represents an RS virus vaccine strain.

TABLE 4

Replication of cpts-RSV 248, cp-RSV, or wild-type RSV A2 in the upper and lower respiratory tract of seronegative chimpanzees

| Animal infected with indicated virus | Route of Inoculation | Chimpanzee number | Virus recovery | | | | | |
|---|---|---|---|---|---|---|---|---|
| | | | Nasopharynx | | Trachea | | Rhinorrhea score | |
| | | | Duration[b] (days) | Peak titer ($\log_{10}$pfu/ml) | Duration[b] (days) | Peak titer ($\log_{10}$pfu/ml) | Mean[c] | Peak |
| cpts-248 | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | |
| cp-RSV | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | |
| A2 wild-type | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | |

[a]IN = Intranasal administration only, at a dose of $10^4$ p.f.u. in a 1.0 ml inoculum; IN + IT = Both intranasal and intratracheal administration, $10^4$ p.f.u. in a 1.0 ml inoculum at each site.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score
[d]Virus isolated only on day indicated.

TABLE 5

Genetic stability of virus present in original nasopharyngeal (NP) swabs or tracheal lavage (TL) specimens obtained from animals experimentally infected with cpts-RSV 248

| Chimpanzee number | NP swab or TL specimen | Virus obtained on post-infection day | Titer of RSV at indicated temperature ($\log_{10}$pfu/ml) | | |
|---|---|---|---|---|---|
| | | | Titer at 32° C. | Titer at 39° C. | Titer at 40° C. |
| 1[a] | NP | 3 | 3.2 | <0.7 | NT |
| | " | 4 | 2.7 | <0.7 | NT |
| | " | 5 | 4.2 | <0.7 | NT |
| | " | 6 | 3.8 | <0.7 | NT |
| | " | 7 | 4.6 | <0.7 | NT |
| | " | 8 | 4.5 | <0.7 | NT |
| | " | 9 | 2.6 | <0.7 | NT |
| | " | 10 | 2.0 | <0.7 | NT |
| | TL | 6 | 5.4 | <0.7 | NT |
| | " | 8 | 2.7 | <0.7 | NT |
| 2[a] | NP | 3 | 3.2 | <0.7 | NT |
| | " | 4 | 3.7 | <0.7 | NT |
| | " | 5 | 4.5 | <0.7 | NT |
| | " | 6 | 4.1 | <0.7 | NT |
| | " | 7 | 3.3 | <0.7 | NT |
| | " | 8 | 4.2 | <0.7 | NT |
| | " | 9 | 2.8 | <0.7 | NT |
| | " | 10 | 1.6 | <0.7 | NT |
| | TL | 6 | 2.2 | <0.7 | NT |
| 3 | NP | 3 | 2.7 | <0.7 | <0.7 |
| | " | 4 | 3.4 | <0.7 | <0.7 |
| | " | 5 | 2.9 | <0.7 | <0.7 |
| | " | 6 | 3.3 | <0.7 | <0.7 |
| | " | 7 | 3.4 | 0.7[b] | <0.7 |
| | " | 8 | 4.7 | 3.5[b] | 2.0[c] |
| | " | 9 | 1.9 | <0.7 | <0.7 |
| | TL | 6 | 1.8 | <0.7 | <0.7 |
| | " | 8 | 1.9 | 1.2[b] | <0.7 |
| | " | 10 | 2.1 | 1.3[b] | <0.7 |
| 4 | NP | 3 | 3.2 | <0.7 | NT |
| | " | 4 | 2.7 | <0.7 | NT |
| | " | 5 | 3.4 | <0.7 | NT |
| | " | 6 | 3.3 | <0.7 | NT |
| | " | 7 | 4.2 | <0.7 | NT |
| | " | 8 | 3.5 | <0.7 | NT |

TABLE 5-continued

Genetic stability of virus present in original nasopharyngeal (NP) swabs or tracheal lavage (TL) specimens obtained from animals experimentally infected with cpts-RSV 248

| Chimpanzee number | Virus obtained NP swab or TL specimen | on post-infection day | Titer of RSV at indicated temperature ($\log_{10}$pfu/ml) | | |
|---|---|---|---|---|---|
| | | | Titer at 32° C. | Titer at 39° C. | Titer at 40° C. |
| | " | 9 | 2.1 | <0.7 | NT |
| | TL | 8 | 2.2 | <0.7 | NT |

NT = Not tested

[a] Isolates (once-passaged virus suspensions with average titer $\log_{10}$pfu/ml of 4.0) were generated for samples from these chimpanzees from each original virus-containing nasopharyngeal swab specimen or trached lavage specimen and tested for efficiency of plaque formation at 32°, 39° and 40° C. No isolate was able to form plaques at 39° C. or 40° C. Isolates from chimpanzees 3 and 4 were not tested in this manner.
[b] The percent titer at 39° C. versus tnat at 32° C.: NP swab day 7 = 0.2%, NP swab day 8 = 6%, TL day day 8 = 20%, TL day 10 = 16%. All plaques were of small-plaque phenotype only; no wild-type size plaques seen.
[c] The percent titer at 40° C. versus that at 32° C. was 0.2%. All plaques were of pinpoint-plaque phenotype; wild-type size plaques were not detected.

TABLE 6

Serum antibody responses of chimpanzees infected with RSV cpts-248, cp-RSV, or RSV A2 wiid-type

| Animals immunized with | Number of chimpanzees | Serum antibody titers (reciprocal mean $\log_2$) | | | | | |
|---|---|---|---|---|---|---|---|
| | | Neutralizing | | ELISA-F | | ELISA-G | |
| | | Day 0 | Day 28 | Day 0 | Day 28 | Day 0 | Day 28 |
| cpts-248 | 4 | <3.3 | 10.7 | 7.3 | 15.3 | 6.3 | 9.8 |
| cp-RSV | 4 | <3.3 | 11.2 | 11.3 | 15.3 | 9.3 | 12.3 |
| RSVM wild-type | 4 | <3.3 | 11.2 | 8.3 | 15.3 | 7.3 | 10.3 | nizing that mutants which are satisfactorily attenuated for the chimpanzee may not be so for seronegative infants and children, the cpts 248 and 530 derivatives, which possess the very uncharacteristic ts mutant properties of restricted replication and attenuation in the upper respiratory tract and a higher level of genetic stability, were further mutagenized.

Progeny viruses that exhibited a greater degree of temperature-sensitivity in vitro than cpts 248 or that had the small plaque phenotype were selected for further study. Mutant derivatives of the cpts 248 that possessed one or more additional ts mutations were produced by 5-fluorouracil mutagenesis (Table 8). Ts mutants that were more temperature-sensitive (ts) than the cpts 248 were identified, and some of these had the small plaque (sp) phenotype. These cpts 248 derivatives were administered to mice. Cpts 248/804, 248/955, 248/404, 248/26, 248/18, and 248/240 mutants were more restricted in replication in the upper and lower respiratory tract of the mouse than their cpts 248 parental virus (Table 9). Thus, viable mutants of cpts 248 which were more attenuated than their cpts 248 were identified, and these derivatives of cpts 248 exhibited a wide range of replicative efficiency in mice, with ts 248/26 being the most restricted. The ts phenotype of the virus present in nasal turbinates and lungs of the mice was almost identical to that of the input virus, indicating genetic stability. A highly attenuated derivative of cpts 248, the cpts 248/404 virus, was 1000-fold more restricted in replication in the nasopharynx compared to wild-type. The cpts 248/404 mutant, possessing at least three attenuating mutations, was also highly restricted in replication in the upper and lower respiratory tracts of four seronegative chimpanzees and infection did not induce rhinorrhea (Table 10). Again, this virus exhibited a high degree of reduction in replication compared to wild-type, being 60,000-fold reduced in the nasopharynx and 100,000-fold in the lungs. Nonetheless, two chimpanzees which were subsequently challenged with RSV wild-type virus were highly resistant (Table 11).

Five small-plaque mutants of cpts-248/404 were derived by chemical mutagenesis in a similar fashion to that

TABLE 7

Immunization of chimpanzees with cpts-248 induces resistance to RSV A2 wild-type virus challenge on day 28

| | | Response to challenge with $10^4$ p.f.u. wild-type virus administered on day 28 | | | | | | | |
|---|---|---|---|---|---|---|---|---|---|
| | | Virus Recovery | | | | Rhinorrhea | | Serum neutralizing antibody titer (reciprocal $\log_2$) on day indicated | |
| Virus used to immunize animal | Chimpanzee number | Nasopharynx | | Trachea | | score | | | |
| | | Peak titer | | Peak titer | | | | | |
| | | Duration (days) | ($\log_{10}$pfu/ml) | Duration (days) | ($\log_{10}$pfu/ml) | Mean[a] | Peak | Day 28 | Day 42 or 56 |
| cpts-248 | 1 | 5 | 2.7 | 0 | <0.7 | 0 | 0 | 10.1 | 11.0 |
| | 2 | 9 | 1.8 | 0 | <0.7 | 0 | 0 | 10.3 | 14.5 |
| cp-RSV | 5 | 5 | 1.0 | 0 | <0.7 | 0 | 0 | 11.1 | 13.3 |
| | 6 | 8 | 0.7 | 0 | <0.7 | 0 | 0 | 11.4 | 12.9 |
| none | 9 | 9 | 5.1 | 13 | 5.4 | 1.0 | 1 | <3.3 | 12.4 |
| | 10 | 9 | 6.0 | 8 | 6.0 | 1.7 | 4 | <3.3 | 13.2 |
| | 11 | 13 | 5.3 | 8 | 5.9 | 2.1 | 3 | <3.3 | 11.6 |
| | 12 | 9 | 5.4 | 8 | 5.6 | 1.0 | 3 | <3.3 | 11.2 |

[a] Mean rhinorrhea score represents the sum of scores during the eight days of peak virus shedding divided by eight. Four is the highest score. A score of zero indicates no rhinorhea detected on any day of the ten-day observation period.

Further Attenuations

Since RS virus produces more symptoms of lower respiratory tract disease in human infants than in the 1–2 year old chimpanzees used in these experimental studies, and recognizing described above. Suspensions of once-amplified plaque progency were screened for the small-plaque (sp) phenotype by plaque titration at 32° C. on HEp-2 cells, and working suspensions of virus were prepared as described above.

Five of the 1785 plaque progeny of the mutagenized cpts-248/404 virus exhibited a stable a phenotype. The shut-off temperature of each mutant was 35° C. or less (Table 12), suggesting that each of these sp derivatives of the cpts-248/404 virus also had acquired an additional ts mutation. Following intranasal inoculation of Balb/c mice with $10^{6.3}$ p.f.u. of a sp derivative of the cpts-248/404, virus could not be detected in the nasal turbinates of mice inoculated with any of these sp derivatives. However, virus was detected in low titer in the lungs in one instance. These results indicate >300-fold restriction of replication in the nasal turbinates and >10,000-fold restriction in lungs compared with wild-type RSV.

Further ts derivatives of the cpts 530 virus were also generated (Table 13). As with the cpts-248 derivatives, the cpts-530 derivatives were more restricted in replication in mice than the cpts-530 parental strain. One mutant, cpts-530/1009, was 30 times more restricted in replication in the nasal turbinates of mice. This cpts-530 derivative is also highly restricted in replication in the upper and lower respiratory tract of seronegative chimpanzees (Table 14). In the nasopharynx, cpts-530 was 30-fold restricted in replication, while cpts-530/1009 was 100-fold restricted compared to wild-type virus. Both of the cpts mutants were highly restricted (20,000 to 32,000-fold) in the lower respiratory tract compared with wild-type virus, even when the mutants were inoculated directly into the trachea. Also, chimpanzees previously infected with cpts-530/1009, cpts-530 or cp-RSV exhibited significant restriction of virus replication in the nasopharynx and did not develop significant rhinorrhea following subsequent combined intranasal and intratracheal challenge with wild-type RSV (Table 15). In addition, chimpanzees previously infected with any of the mutants exhibited complete resistance in the lower respiratory tract to replication of wild-type challenge virus.

These results were completely unexpected based on experience gained during prior studies. For example, the results of an earlier study indicated that the in vivo properties of RSV ts mutants derived from a single cycle of 5-fluorouracil mutagenesis could not be predicted a priori. Moreover, although one of the first four ts mutants generated in this manner exhibited the same shut off temperature for plaque formation as the other mutants, it was overattenuated when tested in susceptible chimpanzees and susceptible infants and young children [Wright et al., *Infect Immun.* 37 (1):397–400 (1982)]. This indicated that the acquisition of the ts phenotype resulting in a 37°–38° C. shut off temperature for plaque formation did not reliably yield a mutant with the desired level of attenuation for susceptible chimpanzees, infants and children. Indeed, the results of studies with heretofore known ts mutants completely fail to provide any basis for concluding that introduction of three independent mutations (or sets of mutations) into RSV by cold-passage followed by two successive cycles of chemical mutagenesis could yield viable mutants which retain infectivity for chimpanzees (and by extrapolation, young infants) and exhibit the desired level of attenuation, immunogenicity and protective efficacy required of a live virus vaccine to be used for prevention of RSV disease.

The above-presented results clearly demonstrate that certain ts derivatives of the cpRSV of the invention have a satisfactory level of infectivity and exhibit a significant degree of attenuation for mice and chimpanzees. These ts mutant derivatives are attenuated and appear highly stable genetically after replication in vivo. These mutants also induce significant resistance to RSV infection in chimpanzees. Thus, these derivatives of cpRSV represent virus strains suitable for use in a live RSV vaccine designed to prevent serious human RSV disease.

TABLE 8

The efficiency of plaque formation of ten mutants derived from RSV cpts-248 by additional 5FU mutagenesis

| Virus | The titer of virus ($\log_{10}$pfu/ml) at the indicated temperature (°C.) | | | | | | | Shut-off temperature (°C.)[1] | Small-plaques at 32 C. |
|---|---|---|---|---|---|---|---|---|---|
| | 32 | 35 | 36 | 37 | 38 | 39 | 40 | | |
| A2 wild-type | 4.5 | 4.6 | 4.4 | 4.5 | 4.5 | 3.8 | 3.8 | >40 | no |
| cp-RSV | 4.7 | 4.4 | 4.3 | 4.3 | 4.2 | 3.7 | 3.5 | >40 | no |
| ts-1 | 5.6 | 5.4 | 4.9 | 4.4 | 2.7 | 2.0 | <0.7 | 38 | no |
| cpts-248 | 3.4 | 3.0 | 2.6* | 1.7** | <0.7 | <0.7 | <0.7 | 38 | no |
| 248/1228 | 5.5* | 5.3* | 5.3** | <0.7 | <0.7 | <0.7 | <0.7 | 37 | yes |
| 248/1075 | 5.3* | 5.3* | 5.1** | <0.7 | <0.7 | <0.7 | <0.7 | 37 | yes |
| 248/965 | 4.5 | 4.2 | 4.2* | <0.7 | <0.7 | <0.7 | <0.7 | 37 | no |
| 248/967 | 4.4 | 3.7 | 3.6* | <0.7 | <0.7 | <0.7 | <0.7 | 37 | no |
| 248/804 | 4.9 | 4.5 | 4.0* | <0.7 | <0.7 | <0.7 | <0.7 | 37 | no |
| 248/955 | 4.8 | 3.7 | 2.8* | <0.7 | <0.7 | <0.7 | <0.7 | 36 | no |
| 248/404 | 3.6 | 2.9* | <0.7 | <0.7 | <0.7 | <0.7 | <0.7 | 36 | no |
| 248126 | 3.1 | 2.9* | <0.7 | <0.7 | <0.7 | <0.7 | <0.7 | 36 | no |
| 248/18 | 4.0* | 4.0** | <0.7 | <0.7 | <0.7 | <0.7 | <0.7 | 36 | yes |
| 248/240 | 5.8* | 5.7** | <0.7 | <0.7 | <0.7 | <0.7 | <0.7 | 36 | yes |

[1]Shut-off temperature is defined as the lowest restrictive temperature at which a fold or greater reduction of plaque titer in HEp-2 cells is observed (bold figures in table).
*Small-plaque phenotype (<50% wild-type plaque size)
**Pinpoint-plaque phenotype (<10% wild-type plaque size)

TABLE 9

Replication and genetic stability of ten mutants derived from RSVcpts-248 in Balb/c mice[1]

| Virus used to infect animal | Shutoff temperature of virus (°C.) | Virus titer (mean $\log_{10}$pfu/g tissue of six animals ± standard error) | | | | | | | |
|---|---|---|---|---|---|---|---|---|---|
| | | Nasal turbinates | | | | Lungs | | | |
| | | 32° C. | 36° C. | 37° C. | 38° C. | 32° C. | 36° C. | 37° C. | 38° C. |
| A2 wild-type | >40 | 5.1 ± 0.15 | 5.2 ± 0.23 | 5.2 ± 0.14 | 5.2 ± 0.27 | 6.1 ± 0.14 | 5.8 ± 0.23 | 6.0 ± 0.12 | 5.9 ± 0.17 |
| cp-RSV | >40 | 4.9 ± 0.20 | 5.1 ± 0.16 | 4.9 ± 0.24 | 4.9 ± 0.22 | 6.0 ± 0.16 | 5.9 ± 0.23 | 5.6 ± 0.15 | 5.6 ± 0.13 |
| ts-1 | 38 | 3.9 ± 0.25 | 2.7 ± 0.27 | 2.4 ± 0.42 | 2.5 ± 0.29 | 4.1 ± 0.21 | 3.5 ± 0.23 | 2.6 ± 0.18 | 2.0 ± 0.23 |
| cpts-248 | 38 | 4.0 ± 0.16 | 2.5 ± 0.34 | <2.0 | <2.0 | 4.4 ± 0.37 | 1.8 ± 0.15 | <1.7 | <1.7 |
| 248/1228 | 37 | 4.1 ± 0.15 | 2.4 ± 0.48 | <2.0 | <2.0 | 2.0 ± 0.37 | <1.7 | <1.7 | <1.7 |
| 248/1075 | 37 | 4.2 ± 0.18 | 2.4 ± 0.40 | <2.0 | <2.0 | 5.5 ± 0.16 | 3.5 ± 0.18 | <1.7 | <1.7 |
| 248/965 | 37 | 3.8 ± 0.23 | <2.0 | <2.0 | <2.0 | 4.5 ± 0.21 | 3.4 ± 0.16 | <1.7 | <1.7 |
| 248/967 | 37 | 4.4 ± 0.20 | <2.0 | <2.0 | <2.0 | 5.4 ± 0.20 | 3.6 ± 0.19 | <1.7 | <1.7 |
| 248/804 | 37 | 2.9 ± 0.19 | <2.0 | <2.0 | <2.0 | 3.6 ± 0.19 | <1.7 | <1.7 | <1.7 |
| 248/955 | 36 | 3.2 ± 0.10 | <2.0 | <2.0 | <2.0 | 3.2 ± 0.22 | <1.7 | <1.7 | <1.7 |
| 248/404 | 36 | 2.1 ± 0.31[2] | <2.0 | <2.0 | <2.0 | 4.4 ± 0.12[2] | 1.8 ± 0.20 | <1.7 | <1.7 |
| 248/26 | 36 | <2.0 | <2.0 | <2.0 | <2.0 | 2.3 ± 0.20 | <1.7 | <1.7 | <1.7 |
| 248/18 | 36 | 2.9 ± 0.99 | <2.0 | <2.0 | <2.0 | 4.3 ± 0.23 | 1.8 ± 0.15 | <1.7 | <1.7 |
| 248/240 | 36 | 2.9 ± 0.82 | <2.0 | <2.0 | <2.0 | 3.9 ± 0.12 | <1.7 | <1.7 | <1.7 |

[1]Mice were administered $10^{6.3}$ p.f.u. intranasally under light anesthesia on day 0, then sacrificed by $CO_2$ asphyxiation on day 4.
[2]In a subsequent study, the level of replication of the cpts-248/404 virus was found to be 2.4 ± 0.24 and 2.6 ± 0.31 in the nasal turbinates and lungs respectively.

TABLE 10

Replication of cpts-RSV 248/404, cpts 248/18, cpts-RSV 248, cp-RSV, or wild-type RSV A2 in the upper and lower respiratory tract of seronegative chimpanzees

| Animal infected with indicated virus | Route of Inoculation | Chimpanzee number | Virus recovery | | | | Rhinorrhea score | |
|---|---|---|---|---|---|---|---|---|
| | | | Nasopharynx | | Trachea | | | |
| | | | Duration[b] (days) | Peak titer ($\log_{10}$pfu/ml) | Duration[b] (days) | Peak titer ($\log_{10}$pfu/ml) | Mean[c] | Peak |
| cpts-248/404 | IN + IT | 13 | 0 | <0.7 | 0 | <0.7 | 0 | 0 |
| | IN + IT | 14 | 0 | <0.7 | 0 | <0.7 | 0 | 0 |
| | IN + IT | 15 | 8 | 1.9 | 0 | <0.7 | 0.3 | 2 |
| | IN + IT | 16 | 9 | 2.0 | 0 | <0.7 | 0.2 | 1 |
| | | | mean 4.3 | mean 4.3 | mean 0 | mean <0.7 | mean 0.1 | mean 0.8 |
| cpts-248# | IN + IT | 1 | 10 | 4.6 | 8[d] | 5.4 | 0.2 | 1 |
| | IN + IT | 2 | 10 | 4.5 | 6 | 2.2 | 0.1 | 1 |
| | IN + IT | 3 | 9 | 4.7 | 10 | 2.1 | 0.1 | 1 |
| | IN + IT | 4 | 9 | 4.2 | 8[d] | 2.2 | 0.1 | 1 |
| | | | mean 9.5 | mean 4.5 | mean 8.0 | mean 3.0 | mean 0.1 | mean 1.0 |
| cp-RSV# | IN | 5 | 20 | 5.3 | 8[d] | 2.9 | 1.0 | 3 |
| | IN | 6 | 16 | 5.8 | 6[d] | 3.0 | 1.8 | 3 |
| | IN + IT | 7 | 13 | 4.3 | 6[d] | 3.0 | 0.6 | 1 |
| | IN + IT | 8 | 16 | 5.0 | 10[d] | 2.8 | 0.5 | 1 |
| | | | mean 16 | mean 5.1 | mean 7.5 | mean 2.9 | mean 1.0 | mean 2.0 |
| A2 wild-type# | IN | 9 | 9 | 5.1 | 13 | 5.4 | 1.0 | 1 |
| | IN | 10 | 9 | 6.0 | 8 | 6.0 | 1.7 | 4 |
| | IN + IT | 11 | 13 | 5.3 | 8 | 5.9 | 2.1 | 3 |
| | IN + IT | 12 | 9 | 5.4 | 8 | 5.6 | 1.0 | 3 |
| | | | mean 10 | mean 5.5 | mean 9.3 | mean 5.7 | mean 1.4 | mean 2.8 |

[a]IN = Intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
These are the same animals included in Tables 4 and 7.

TABLE 11

Immunization of chimpanzees with cpts-248/404 induces resistance to RSV A2 wild-type virus challenge on day 28.

| Virus used to immunize animal | Chimpanzee number | Virus Recovery | | | | Rhinorrhea scores | | Serum neutralizing antibody titer (reciprocal $\log_2$) on day indicated[b] | |
|---|---|---|---|---|---|---|---|---|---|
| | | Nasopharynx | | Tracheal lavage | | | | | |
| | | Duration (days) | Peak titer ($\log_{10}$pfu/ml) | Duration (days) | Peak titer ($\log_{10}$pfu/ml) | Mean[a] | Peak | Day 28 | Day 49 or 56 |
| cpts-248/404 | 13 | 0 | <0.7 | 0 | <0.7 | 0 | 0 | 7.9 | 9.0 |
| | 14 | 8 | 3.4 | 0 | <0.7 | 0 | 0 | 7.0 | 12.5 |
| | | mean 4.0 | mean 2.0 | mean 0 | mean <0.7 | mean 0 | mean 0 | mean 7.5 | mean 10.8 |
| cpts-248# | 1 | 5 | 2.7 | 0 | <0.7 | 0 | 0 | 11.5 | 13.0 |
| | 2 | 9 | 1.8 | 0 | <0.7 | 0 | 0 | 12.7 | 14.5 |
| | | mean 7.0 | mean 2.3 | mean 0 | mean <0.7 | mean 0 | mean 0 | mean 12.1 | mean 13.8 |
| cp-RSV# | 5 | 5 | 1.0 | 0 | <0.7 | 0 | 0 | 12.2 | 11.1 |
| | 6 | 8 | 0.7 | 0 | <0.7 | 0 | 0 | 11.9 | 9.9 |
| | | mean 6.5 | mean 0.9 | mean 0 | mean <0.7 | mean 0 | mean 0 | mean 12.1 | mean 10.5 |
| None# | 9 | 9 | 5.1 | 13 | 5.4 | 1.0 | 1 | <3.3 | 11.0 |
| | 10 | 9 | 6.0 | 8 | 6.0 | 1.7 | 4 | <3.3 | 9.8 |
| | 11 | 13 | 5.3 | 8 | 5.9 | 2.1 | 3 | <3.3 | 9.4 |
| | 12 | 9 | 5.4 | 8 | 5.6 | 1.0 | 3 | <3.3 | 14.5 |
| | | mean 10 | mean 5.5 | mean 9.2 | mean 5.7 | mean 1.4 | mean 2.8 | mean <3.3 | mean 11.2 |

[a]Mean rhinorrhea score represents the sum of scores duting the eight days of peak virus sheeding divided by eight. Four is the highest score.
These are the same animals included in Tables 4, 7, and 10.
[b]Serum nuetralizing titers in this table, including those from animals previously described, were determined simultaneously in one assay.

TABLE 12

The efficiency of plaque formation and replication in Balb/c mice of five small-plaque derivatives of RSV cpts-248/404.
Efficiency of plaque formation tested in HEp-2 cells at permissive and restrictive temperatures

| Virus | The titer of virus ($\log_{10}$pfu/ml) at the indicated temperature (°C.) | | | | | | | Shut-off temp. (°C)[1] | Small-plaques at 32° C. | Replication in Balb/c mice[2] | |
|---|---|---|---|---|---|---|---|---|---|---|---|
| | 32 | 35 | 36 | 37 | 38 | 39 | 40 | | | Nasal turbinates[3] | Lungs[3] |
| A2 wild-type | 6.0 | 6.1 | 6.0 | 5.8 | 5.9 | 5.4 | 5.4 | >40 | no | 4.5 ± 0.34 | 5.6 ± 0.13 |
| cp-RSV | 6.2 | 6.2 | 6.0 | 6.0 | 5.9 | 5.6 | 5.4 | >40 | no | 4.5 ± 0.10 | 5.3 ± 0.20 |
| cpts-248 | 7.5 | 7.3 | 6.2** | 5.3** | <0.7 | <0.7 | <0.7 | 37 | no | 3.3 ± 0.35 | 4.8 ± 0.14 |
| 248/404 | 5.5 | 3.6** | <0.7 | <0.7 | <0.7 | <0.7 | <0.7 | 36 | no | 2.4 ± 0.24 | 2.6 ± 0.31 |
| 248/404/774 | 2.9* | <0.7 | <0.7 | <0.7 | <0.7 | <0.7 | <0.7 | ≦35 | yes | <2.0 | 1.8 ± 0.24 |
| 248/404/832 | 5.5** | <0.7 | <0.7 | <0.7 | <0.7 | <0.7 | <0.7 | ≦35 | yes | <2.0 | <1.7 |
| 248/404/886 | 5.0** | <0.7 | <0.7 | <0.7 | <0.7 | <0.7 | <0.7 | ≦35 | yes | <2.0 | <1.7 |
| 248/404/893 | 5.4** | <0.7 | <0.7 | <0.7 | <0.7 | <0.7 | <0.7 | ≦35 | yes | <2.0 | <1.7 |
| 248/404/1030 | 4.4* | <0.7 | <0.7 | <0.7 | <0.7 | <0.7 | <0.7 | 35 | yes | <2.0 | <1.7 |

[1]Shut-off temperature is defined as the lowest restrictive temperature at which a 100-fold or greater reduction of plaque titer is observed bold figures in table).
[2]Mice were administered $10^{6.3}$ p.f.u. intranasally under light anesthesia on day 0, then sacrificed by $CO^2$ asphyxiation on day 4 when tissues were harvested for virus titer.
[3]Mean $\log_{10}$pfu/g tissue of six animals ± standard error.
*Small-plaque phenotype (<50% wild-type plaque size).
**Pinpoint-plaque phenotype (<10% wild-type plaque size).

TABLE 13

The efficiency of plaque formation and level of replication in mice of 14 mutants derived from RSV cpts-530, compared with controls

| RSV | In vitro efficiency of plaque formation The titer of virus ($\log_{10}$pfu/ml) at the indicated temperature (°C.) | | | | | | | | Shut-off Temp. (°C.)[1] | Replication in mice[2] (mean $\log_{10}$pfu/g tissue of six animals ± SE) | |
|---|---|---|---|---|---|---|---|---|---|---|---|
| | 32 | 34 | 35 | 36 | 37 | 38 | 39 | 40 | | Nasal turbinates | Lungs |
| A2 | 6.3 | 6.3 | 6.3 | 6.2 | 6.3 | 6.3 | 6.1 | 5.6 | >40 | 5.0 ± 0.14 | 5.8 ± 0.05 |
| cp-RSV | 6.5 | 6.2 | 6.2 | 6.2 | 6.1 | 6.0 | 6.1 | 5.6 | >40 | n.d. | n.d. |
| cpts-248 | 6.3 | 6.3 | 6.3 | 6.3 | 3.7** | <0.7 | <0.7 | <0.7 | 37/38 | 4.1 ± 0.08 | 5.1 ± 0.13 |
| 248/404 | 6.3 | 5.7* | 4.3** | <0.7 | <0.7 | <0.7 | <0.7 | <0.7 | 35/36 | 2.1 ± 0.19 | 3.6 ± 0.10 |

TABLE 13-continued

The efficiency of plaque formation and level of replication in mice of 14 mutants derived from RSV cpts-530, compared with controls

| | In vitro efficiency of plaque formation The titer of virus ($\log_{10}$pfu/ml) at the indicated temperature (°C.) | | | | | | | | Shut-off Temp. (°C.)[1] | Replication in mice[2] (mean $\log_{10}$pfu/g tissue of six animals ± SE) | |
|---|---|---|---|---|---|---|---|---|---|---|---|
| RSV | 32 | 34 | 35 | 36 | 37 | 38 | 39 | 40 | | Nasal turbinates | Lungs |
| cpts-530 | 6.2 | 6.3 | 6.2 | 6.1 | 6.2* | 5.5** | <0.7 | <0.7 | 39 | 3.4 ± 0.09 | 4.3 ± 0.14 |
| 530/346 | 5.9 | 5.9 | 5.7 | 4.7 | 3.5 | <0.7 | <0.7 | <0.7 | 37 | 3.3 ± 0.11 | 4.7 ± 0.09 |
| 530/977 | 5.0 | 4.4 | 3.6 | 3.4 | 2.8* | <0.7 | <0.7 | <0.7 | 37 | 3.4 ± 0.11 | 2.7 ± 0.05 |
| 530/9 | 6.0 | 5.6 | 5.0 | 3.5* | 3.5** | <0.7 | <0.7 | <0.7 | 36 | 2.1 ± 0.06 | 3.5 ± 0.08 |
| 530/1009 | 4.8 | 4.0 | 3.7* | 2.0** | 1.5** | <0.7 | <0.7 | <0.7 | 36 | 2.2 ± 0.15 | 3.5 ± 0.13 |
| 530/667 | 5.5 | 4.9 | 4.5* | 2.0** | 0.7 | <0.7 | <0.7 | <0.7 | 36 | 2.4 ± 0.12 | 2.9 ± 0.15 |
| 530/1178 | 5.7 | 4.0 | 5.5 | 3.7** | 2.0** | <0.7 | <0.7 | <0.7 | 36 | 3.3 ± 0.06 | 42 ± 0.11 |
| 530/464 | 6.0 | 5.0* | 4.7* | 1.8** | <0.7 | <0.7 | <0.7 | <0.7 | 36 | <2.0 | 2.6 ± 0.10 |
| 530/403 | 5.7 | 5.1 | 4.3 | 2.9 | <0.7 | <0.7 | <0.7 | <0.7 | 36 | <2.0 | <1.7 |
| 530/1074 | 5.1 | 4.6 | 4.1* | <0.7 | <0.7 | <0.7 | <0.7 | <0.7 | 36 | 3.0 ± 0.13 | 3.8 + 0.13 |
| 530/963 | 5.3 | 5.0 | 4.2* | 0.7 | <0.7 | <0.7 | <0.7 | <0.7 | 36 | 2.0 ± 0.05 | <1.7 |
| 530/653 | 5.4 | 5.1 | 4.5 | <0.7 | <0.7 | <0.7 | <0.7 | <0.7 | 36 | 2.2 ± 0.10 | 3.1 ± 0.16 |
| 530/1003 | 5.6 | 4.1 | 2.5 | 2.1** | <0.7 | <0.7 | <0.7 | <0.7 | 35 | <2.0 | <1.7 |
| 530/1030 | 4.3 | 3.7* | 1.7** | <0.7 | <0.7 | <0.7 | <0.7 | <0.7 | 35 | <2.0 | 1.8 + 0.13 |
| 530/188 | 5.0* | 1.0* | 1.0 | <0.7 | <0.7 | <0.7 | <0.7 | <0.7 | ≦34 | <2.0 | <1.7 | n.d. = not done
*Small-plaque phenotype (<50% wild-type plaque size)
**Pinpoint-plaque phenotype (<10% wild-type plaque size)
[1]Shut-off temperature is defined as the lowest restrictive temeprature at which a 100-fold or greater reduction of plaque titer is observed (bold figures in table).
[2]Mice were administered $10^{6.3}$ p.f.u. intranasally under light anesthesia on day 0, then sacrificed by $CO_2$ asphyxiation on day 4.

TABLE 14

Replication of cpts-530/1009, cpts-RSV 530, cp-RSV, or wild-type RSV A2 in the upper and lower respiratory tract of seronegative chimpanzees induces serum neutralizing antibodies.

| Animal infected with $10^4$ pfu of indicated virus | Route of inoculation | Chimpanzee number | Virus replication | | | | Rhinorrhea scores | | Day 28 reciprocal serum neutralizing antibody titers[g] |
|---|---|---|---|---|---|---|---|---|---|
| | | | Nasopharynx | | Trachea | | | | |
| | | | Duration[b] (days) | Peak titer ($\log_{10}$pfu/ml) | Duration[b] (days) | Peak titer ($\log_{10}$pfu/ml) | Mean[c] | Peak | |
| pts-530/1009 | IN + IT | 1 | 9 | 3.1 | 0 | <1.0 | 0.5 | 2 | 1,097 |
| | IN + IT | 2 | 10 | 4.0 | 10[e] | 1.8 | 0.5 | 2 | 416 |
| | IN + IT | 3 | 9 | 4.0 | 0 | <1.0 | 0.8 | 2 | 1,552 |
| | IN + IT | 4 | 9 | 3.3 | 0 | 4.0 | 0.4 | 1 | 1,176 |
| | | | mean 9.3 | mean 3.6 | mean 2.5 | mean 1.2 | mean 0.5 | mean 1.3 | mean 1,060 |
| cpts-530 | IN + IT | 5 | 9 | 3.5 | 4e | 2.6 | 0.3 | 1 | 10,085 |
| | IN + IT | 6 | 9 | 5.2 | 0 | <1.0 | 1.1 | 3 | 3,566 |
| | IN + IT | 7 | 8 | 33 | 0 | <1.0 | 0.6 | 2 | 588 |
| | IN + IT | 8 | 8 | 4.4 | 0 | <1.0 | 0.5 | 2 | 1,911 |
| | | | mean 8.5 | mean 4.1 | mean 1.0 | mean 1.4 | mean 0.6 | mean 2.0 | mean 4,038 |
| cp-RSV | IN | 9[d] | 20 | 5.3 | 8[e] | 2.9 | 1.0 | 3 | 416 |
| | IN | 10[d] | 16 | 5.8 | 6[e] | 3.0 | 1.8 | 3 | 2,048 |
| | IN + IT | 11[d] | 13 | 4.3 | 6[e] | 3.0 | 0.6 | 1 | 776 |
| | IN + IT | 12[d] | 16 | 5.0 | 10[e] | 2.8 | 0.5 | 1 | 891 |
| | | | mean 16 | mean 5.1 | mean 7.5 | mean 2.9 | mean 1.0 | mean 2.0 | mean 1,033 |
| A2 wild-type | IN | 13[f] | 9 | 5.1 | 13 | 5.4 | 1.0 | 1 | 1,351 |
| | IN | 14[f] | 9 | 6.0 | 8 | 6.0 | 1.7 | 4 | 676 |
| | IN + IT | 15[d] | 13 | 5.3 | 8 | 5.9 | 2.1 | 3 | 1,261 |
| | IN + IT | 16[d] | 9 | 5.4 | 8 | 5.6 | 1.0 | 3 | 20,171 |
| | | | mean 10 | mean 5.5 | mean 9.3 | mean 5.7 | mean 1.4 | mean 2.8 | mean 5,865 |

[a]IN = Intranaaal only; IN + IT = Both intranasal and intratracheal adminiatration.
[b]Indicated last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Animals from Crowe, et al. Vaccine 12:691–699 (1994).
[e]Virus isolated only on day indicated.
[f]Animals from Collins, et al. Vaccine 8:164–168 (1990).
[g]*Determined by complement-enhanced 60% plaque reduction of RSV A2 in HEp-2 cell monolayer cultures. All titers were determined simultaneously in a single assay. The reciprocal titer of each animal on day 0 was <10.

TABLE 15

Immunization of chimpanzees with cpts-530/1009 or cpts-530 induces resistance to wild-type RSV A2 virus challenge on day 28.

| Virus used for immunization | Chimpanzee number | Virus replication | | | | Rhinorrhea scores | | Serum neutralizing antibody (reciprocal $\log_2$) on day indicated[d] | |
|---|---|---|---|---|---|---|---|---|---|
| | | Nasopharynx | | Tracheal lavage | | | | | |
| | | Duration (days) | Peak titer ($\log_{10}$pfu/ml) | Duration (days) | Peak titer ($\log_{10}$pfu/ml) | Mean[a] | Peak | Day 28 | Day 49 or 56 |
| cpts-530/1009 | 3 | 7 | 2.1 | 0 | <0.7 | 0 | 0 | 1,552 | 3,823 |
| | 4 | 0 | <0.7 | 0 | <0.7 | 0 | 0 | 1,176 | 1,911 |
| cpts-530 | 5 | 0 | <0.7 | 0 | <0.7 | 0 | 0 | 10,085 | 6,654 |
| | 6 | 0 | <0.7 | 0 | <0.7 | 0.3 | 2 | 3,566 | 1,911 |
| cp-RSV | 11[b] | 5 | 1.0 | 0 | <0.7 | 0 | 0 | 776 | 2,048 |
| | 12[b] | 8 | 0.7 | 0 | <0.7 | 0 | 0 | 891 | 1,783 |
| none | 13[b] | 9 | 5.1 | 13 | 5.4 | 0 | 1 | <10 | 1,351 |
| | 14[b] | 9 | 6.0 | 8 | 6.0 | 1.7 | 4 | <10 | '676 |
| | 15[c] | 13 | 5.3 | 8 | 5.9 | 2.1 | 3 | <10 | 1,261 |
| | 16[c] | 9 | 5.4 | 8 | 5.6 | 1.0 | 3 | <10 | 20,171 |

[a]Mean rhinorrhea scores represent the sum of scores during the eight days of peak virus shedding divided by eight. Four is the highest score.
[b]Animals from Crowe et al. Vaccine 12:691–699 (1994).
[c]Animals from Collins et al. Vaccine 8:164–168 (1990).
[d]Serum netralizing titers in this table, including those from animals previously described, were determined simultaneously in one assay.

Effect of Passively-Acquired Serum RSV Antibodies on cpts Mutants in Chimpanzees In order to examine the effect of passively-acquired serum RSV antibodies on attenuation, immunogenicity and protective efficacy of various cpts mutants of the invention in chimpanzees, the in vivo replication of cpts-248, cpts-248/404, and cpts-530/1009, was evaluated in seronegative chimpanzees which were infused with RSV immune globulin two days prior to immunization (Table 16). Antibody was passively transferred in order to simulate the conditions which obtain in young infants who possess maternally-derived RSV antibodies. In this way, it was possible to assess the immunogenicity of each indicated mutant in the presence of passive RSV antibodies to determine whether the replication, of highly attenuated viruses might be so reduced in infants with a moderate to high titer of passive antibodies as to preclude the induction of a protective immune response. It would also be possible to define the nature of the antibody response to immunization in the presence of passively acquired antibodies, and to define the extent and functional activity of the antibody response to virus challenge. The level of virus replication in the nasopharynx and the associated clinical score for the attenuated mutants was either not altered or only moderately altered by the presence of serum RSV antibodies when the infection of those animals was compared to that of non-infused seronegative chimpanzees. In contrast, the presence of passively-acquired antibodies effectively prevented virus replication of cpts-248 in the lower respiratory tract. Because the other two mutants were already highly restricted in the lungs, the similar effect of passive antibodies could not be evaluated against these mutants.

Infusion of human RSV immune globulin yielded moderately high serum levels of RSV F antibodies (titer 1:640 to 1:1600), and neutralizing antibodies (titer 1:199 to 1:252), but not appreciable amounts of serum RSV G antibody detectable above background (Table 17). Chimpanzees who were infused with human RSV antibodies prior to immunization with cpts-248/404, cpts-530/1009, or cpts-248 developed only one-tenth the quantity of RSV F antibodies and about one-half the titer of neutralizing antibodies by day 42 post-immunization, compared to non-infused immunized animals tested 28 days post-immunization. Because the infused human IgG contained substantial amounts of RSV F and RSV neutralizing antibodies, the residual antibodies from the infusion present in the 42-day serum samples could not be distinguished from antibodies produced de novo in response to immunization. Given the normal half-life of human serum IgG antibodies in chimpanzees (Prince et al., Proc. Natl. Acad. Sci. USA 85:6944–6948), the observed levels of F and neutralizing antibodies on day 42 following immunization with cpts are higher than would be predicted for a residuum of the infusion. In addition, the RSV G antibody response following immunization of the infused animals confirms that these chimpanzees mounted an immune response to immunization.

Four to six weeks following immunization the chimpanzees were challenged with wild-type RSV. Each of the animals exhibited complete resistance in their lower respiratory tract, whether or not human IgG was infused two days before immunization (Table 18). Non-infused animals developed a modest neutralizing antibody response to challenge or none at all (Table 17). In contrast, the infused chimpanzees uniformly developed an unusually high titer of RSV neutralizing antibodies in response to wild-type virus challenge despite the fact that virus replication had been severely restricted (Tables 17 and 18). Moreover, following immunization in the presence of antibodies the most attenuated virus, cpts-248/404, which exhibited the lowest level of virus replication during immunization, had the highest post-challenge neutralizing antibody titers (Table 17). In contrast, the least attenuated virus, cpts-248, had the lowest post-challenge neutralizing antibody titer of the three groups of infused animals. In addition to an increase in the quantity of the antibodies induced by immunization in the presence of antibodies, the quality of the antibodies, as measured by the neutralizing to ELISA F antibody titer ratio, was significantly greater than that induced by immunization in seronegative animals (Table 17). The neutralizing/ELISA F ratio of the antibodies produced in the infused/immunized animals post-challenge was about 10- to 20-fold higher than in the non-infused animals and was consistent in all groups, regardless of mutant used to immunize (Table 17).

The presence of passively-acquired antibodies at the time of immunization with a live virus vaccine might alter the immune response to vaccine in three distinct ways. First, a significant decrease in the level of replication of vaccine virus might occur that results in decreased immunogenicity. It is possible that the passively-transferred RSV antibodies could restrict the replication of the vaccine viruses, especially the most defective mutants, and greatly decrease their immunogenicity. The results presented herein indicate that replication of the least attenuated mutant (cpts-248) in the lower respiratory tract was indeed abrogated by the presence of passively-acquired serum IgG RSV antibodies, whereas replication in the upper respiratory tract did not appear to be significantly affected. The replication of the least attenuated mutant tested, cpts-248, was ≧200-fold more (i.e. completely) restricted in the lower respiratory tract in the presence of antibodies. The level of replication of the more attenuated mutants, cpts-530/1009 and cpts-248/404, in the lower respiratory tract was highly restricted even in the seronegative animals. Therefore, a significant effect of passive antibodies on virus replication could not be detected. Immunization with each of the three attenuated mutants induced a high degree of protection against wild-type challenge in both the upper and lower respiratory tracts, whether or not passively-acquired RSV antibodies were present at the time of immunization. Thus, the level of replication of the vaccine viruses in the upper respiratory tract of passively-immunized chimpanzees was sufficient to induce a high level of resistance to wild-type virus challenge which was comparable to that induced in non-infused animals.

Second, passive antibodies can alter the immune response to infection by causing a decrease in the amount and functional activity of antibodies that are induced. For this reason the magnitude and the character of the antibody response to live virus immunization in the presence of passive antibodies was analyzed. Postimmunization serum ELISA IgG F antibody titers of immunized, infused animals were 10-fold lower than the postimmunization F titers of non-infused seronegative animals. The serum RSV neutralizing antibody response was also slightly decreased in those animals, on average being 2-fold lower than in non-infused animals. Because some of the ELISA F and neutralizing antibodies detected postimmunization represent residual antibodies from the infusion, the actual decrease of the neutralizing and F antibody response caused by preexisting antibodies is probably even more significant than is apparent. Moreover, the human immune globulin preparation used contained a low level of antibodies to the G glycoprotein of RSV (Table 17). This permitted an examination of the IgG RSV G glycoprotein antibody response of the chimpanzees to infection with the candidate vaccine viruses. The G antibody responses demonstrated at least a 4-fold or greater increase, indicating that each of the passively-immunized animals was infected by vaccine virus, including chimpanzees immunized with cpts-248/404 which did not shed virus. The magnitude of the G antibody response to immunization did not appear to be adversely influenced by the passively transferred antibodies.

Thirdly, the antibody response to RSV wild-type virus challenge of animals immunized in the presence of passively-acquired antibodies could be altered. Chimpanzees immunized in the absence of infused antibodies exhibited significant resistance to subsequent RSV challenge. In addition, these animals failed to develop an appreciable antibody response to challenge virus. Although each of the 6 infused, immunized animals also exhibited significant resistance to RSV, a greatly enhanced antibody response to challenge was observed. Post-challenge F or G antibody levels in the treated animals immunized with cpts-530/1009 or cpts-248/404 were increased at least 10-fold, while the neutralizing antibody response represented as much as an 800-fold increase. These results suggest that repeated immunization of infants possessing maternal antibodies with live attenuated mutants beginning very early in life might stimulate effective resistance and an associated enhanced secondary antibody response of high quality. The mechanism responsible for an enhanced immune response to second infection in the absence of appreciable replication of the challenge virus is not understood. The presence of serum antibodies at the time of immunization, while allowing a modest antibody response to immunization in infused animals, favors the development of a B cell repertoire that elaborates antibodies of highly functional activity following subsequent RSV challenge.

The results reported herein are highly significant in that for the first time live attenuated RSV virus vaccine has been shown to be efficacious in an animal model which mimics the target population for an RSV vaccine, i.e. the four to six week old infant having passively acquired RSV neutralizing antibodies as a result of transplacental transfer from the mother. The importance of this finding is clear from the fact that, as discussed, supra, the high expectation that the passively transferred RSV antibodies would have inhibited the replication of the cpts vaccine, rendering it non-immunogenic and non-protective has, suprisingly, not been borne out.

TABLE 16

Replication of RSV cpts-248/404, cpts-248, or cpts-530/1009 in the upper and lower respiratory tract of seronegative chimpanzee, some of which were infused with RSV neutralizing antibodies two days prior to immunization.

| Animal infected with $10^4$ pfu of indicated virus | Reciprocal serum RSV neutralizing antibody titer at time of immunization | Chimpanzee number | Virus replication | | | | Rhinorrhea score | |
|---|---|---|---|---|---|---|---|---|
| | | | Nasopharynx | | Trachea | | | |
| | | | Duration (days) | Peak titer ($\log_{10}$pfu/ml) | Duration (days) | Peak titer ($\log_{10}$pfu/ml) | Peak | Mean |
| cpts-248/404 | <10 | 17 | 0 | <0.7 | 0 | <0.7 | 0 | 0 |
| | <10 | 20 | 9 | <0.7 | 0 | <0.7 | 0 | 0 1' |
| | <10 | 19 | 8 | 1.9 | 0 | <0.7 | 2 | 0.3 |
| | <10 | 20 | 9 | 2.0 | 0 | <0.7 | 1 | 0.2 |
| | | | (mean 4.3) | (mean 1.3) | (mean 0) | (mean <0.7) | (mean 0.8) | (mean 0.1) |
| | 142 | 21 | 0 | <0.7 | 0 | <0.7 | 2 | 0.6 |

TABLE 16-continued

Replication of RSV cpts-248/404, cpts-248, or cpts-530/1009 in the upper and lower respiratory tract of seronegative chimpanzee, some of which were infused with RSV neutralizing antibodies two days prior to immunization.

| Animal infected with $10^4$ pfu of indicated virus | Reciprocal serum RSV neutralizing antibody titer at time of immunization | Chimpanzee number | Virus replication Nasopharynx Duration (days) | Peak titer ($\log_{10}$pfu/ml) | Trachea Duration (days) | Peak titer ($\log_{10}$pfu/ml) | Rhinorrhea score Peak | Mean |
|---|---|---|---|---|---|---|---|---|
| | 256 | 22 | 0 | <0.7 | 0 | <0.7 | 1 | 0.1 |
| | | | (mean 0) | (mean <0.7) | (mean 0) | (mean <0.7) | (mean 1.5) | (mean 0.4) |
| cpts-530/1009 | <10 | 1 | 9 | 3.1 | 0 | <1.0 | 1 | 0.3 |
| | <10 | 2 | 10 | 4.0 | 10 | 1.8 | 1 | 1.1 |
| | <10 | 3 | 9 | 4.0 | 0 | <1.0 | 1 | 0.6 |
| | <10 | 4 | 9 | 3.3 | 0 | <1.0 | 1 | 0.5 |
| | | | (mean 9.3) | (mean 3.6) | (mean 2.5) | (mean 1.2) | (mean 1.0) | (mean 0.6) |
| | 259 | 23 | 8 | 3.0 | 0 | <0.7 | 1 | 0.1 |
| | 190 | 24 | 7 | 1.2 | 0 | <0.7 | 1 | 0.2 |
| | | | (mean 7.5) | (mean 2.1) | (mean 0) | (mean <0.7) | (mean 1.0) | (mean 0.2) |
| cpts-248 | <10 | 25 | 10 | 4.6 | 8 | 5.4 | 1 | 0.2 |
| | <10 | 26 | 10 | 4.5 | 6 | 2.2 | 1 | 0.1 |
| | <10 | 27 | 9 | 4.7 | 10 | 2.1 | 1 | 0.1 |
| | <10 | 28 | 9 | 4.2 | 8 | 2.2 | 1 | 0.1 |
| | | | (mean 9.5) | (mean 4.5) | (mean 8.0) | (nean 3.0) | (mean 1.0) | (mean 0.1) |
| | 290 | 29 | 13 | 4.2 | 0 | <0.7 | 2 | 0.4 |
| | 213 | 30 | 16 | 4.7 | 0 | <0.7 | 3 | 0.9 |
| | | | (mean 14.5) | (mean 4.5) | (mean 0) | (mean <0.7) | (mean 2.5) | (mean 0.7) |

TABLE 17

Serum antibody response of chimpanzees immunized on day 0 with RSV cpts-248/404, cpts-248, or cpts-530/1009, in the presence or absence of passively-transferred antibodies, and challenged 4 to 6 weeks later with wild-type RSV A2.

| Animal infected with indicated virus | No. of animals | Infused with antibodies | Serum antibody titer (reciprocal of geometric mean) | | | | | | | | | | | | Post-challenge neut./ELISA antibody titer ratio | |
|---|---|---|---|---|---|---|---|---|---|---|---|---|---|---|---|---|
| | | | IgG ELISA | | | | | | | | Neutralizing[3] | | | | | |
| | | | RSV F | | | | RSV G | | | | | | | | | |
| | | | Prior to study | Day 0 (48 hrs. after infusion of antibodies) | Post-immunization[1] | 28 days post-challenge[2] | Prior to study | Day 0 (48 hrs. after infusion of antibodies) | Post-immunization[1] | 28 days post-challenge[2] | Prior to study | Day 0 (48 hrs. after infusion of antibodies) | Post-immunization[1] | 28 days post-challenge[2] | F | G |
| cpts-248/404 | 4 | no | <40 | <40 | 6,400 | 2,560 | 60 | 60 | 1,000 | 1,600 | <10 | <10 | 208 | 362 | 0.2 | 0.1 |
| | 2 | yes | <40 | 1,600 | 640 | 25,600 | 100 | 100 | 1,600 | 21,760 | <10 | 199 | 111 | 92,681 | 4.3 | 3.6 |
| cpts-530/1009 | 4 | no | <40 | <40 | 6,400 | 10,240 | <40 | <40 | 10,240 | 2,560 | <10 | <10 | 256 | 2521 | 1.0 | 03 |
| | 2 | yes | <40 | 1,600 | 640 | 10,240 | 40 | 100 | 400 | 10,240 | <10 | 225 | 52 | 37,641 | 3.7 | 3.7 |
| cpts-248 | 4 | no | <40 | <40 | 7,840 | 6,400 | <40 | <40 | 250 | 2,560 | <10 | <10 | 147 | 338 | 0.1 | 0.1 |
| | 2 | yes | <40 | 640 | 1,600 | 5,400 | 40 | 40 | 1,600 | 5,440 | <10 | 252 | 119 | 26,616 | 4.9 | 4.9 |

[1]The day on which postimmunization titer was determined was also the day on which challenge was performed, i.e. day 28 for animals not infused with antibody, day 42 for animals infused.
[2]Values determined from samples taken 28 days after challenge. Challenge performed on day 28 postimmunization for animals not infused with antibody, day 42 for animals infused.
[3]Determined by complement-enhanced 60% plaque reduction of RSV A2 in HEp-2 cell monolayer cultures.
Neutralizing antibody titer represents the mean value from two tests.

TABLE 18

Immunization of chimpanzees with RSV cpts-248, cpts-248/404, or cpts-530/1009 induces resistance to wild-type RSV A2 challenge 4–6 weeks later.

| Virus used for immunization | Passively-transferred RSV antibodies present | Chimpanzee number | Replication of RSV A2 challenge virus[a] | | | | Rhinorrhea score | |
|---|---|---|---|---|---|---|---|---|
| | | | Nasopharynx | | Tracheal lavage | | | |
| | | | Duration (days) | Peak titer ($\log_{10}$pfu/ml) | Duration (days) | Peak titer ($\log_{10}$pfu/ml) | Mean[b] | Peak |
| cpts-248/404 | no | 17[c] | 0 | <0.7 | 0 | <0.7 | 0 | 0 |
| | no | 19[c] | 8 | 3.4 | 0 | <0.7 | 0 | 0 |
| | yes | 21 | 6 | 2.7 | 0 | <0.7 | 0.5 | 2 |
| | yes | 22 | 0 | <0.7 | 0 | <0.7 | 0 | 0 |
| cpts-530/1009 | no | 1 | 7 | 2.1 | 0 | <0.7 | 0 | 0 |
| | no | 2 | 0 | <0.7 | 0 | <0.7 | 0 | 0 |
| | yes | 23 | 6 | 2.5 | 0 | <0.7 | 0.5 | 1 |
| | yes | 24 | 7 | 2.0 | 0 | <0.7 | 0.2 | 1 |
| cpts-248 | no | 25[c] | 5 | 2.7 | 0 | <0.7 | 0 | 0 |
| | no | 26[c] | 9 | 1.8 | 0 | <0.7 | 0 | 0 |
| | yes | 29 | 0 | <0.7 | 0 | <0.7 | 0 | 0 |
| | yes | 30 | 6 | 2.4 | 0 | <0.7 | 1.2 | 3 |
| none | no | 13[d] | 9 | 5.1 | 13 | 5.4 | 1.0 | 1 |
| | no | 14[d] | 9 | 6.0 | 8 | 6.0 | 1.7 | 4 |
| | no | 15[c] | 13 | 5.3 | 8 | 5.9 | 2.1 | 3 |
| | no | 16[c] | 9 | 5.4 | 8 | 5.6 | 1.0 | 3 |

[a]Animals which were immunized with indicated virus 4 to 6 weeks prior were challenged with $10^4$ pfu of RSV A2 wild-type virus.
[b]Mean rhinorrhea scores represent the sum of scores during the eight days of peak virus shedding divided by eight. Four is the highest score: zero is the lowest score and represents complete absence of detectable rhinorrhea.
[c]Animals from Crowe et al. Vaccine 12:691–699 (1994).
[d]Animals from Collins et al.. Vaccine 8:164–168 (1990).

EXAMPLE II

Use of Cold Adaptation to Attenuate cpRSV Mutants

This Example describes the introduction of growth restriction mutations into incompletely attenuated host range-restricted cpRSV strains by further passage of the strains at increasingly reduced temperatures to produce derivative strains which are more satisfactorily attenuated for use in human vaccines.

These cold-adaptation (ca) approaches were used to introduce further attenuation into the cpRSV 3131 virus, which is incompletely attenuated in seronegative children.

Under the first strategy, a parent stock of cold-passaged RSV A2 (cpRSV 3131) obtained from Flow Laboratories was prepared by passage in MRC-5 cells at 25° C. as described in Example I. Briefly, cold-passaged virus was inoculated into MRC-5 or Vero cell monolayer culture at a multiplicity of infection of $\leq 0.01$ and the infected cells were incubated for 3 to 14 days before subsequent passage. Virus was passaged over 20 times at 20°–22° C. to derive more attenuated virus. The technique of rapid passage, as soon as the first evidence of virus replication is evident (i.e., 3 to 5 days), was preferable for selection of mutants able to replicate efficiently at low temperatures. Additionally, an RSV subgroup B strain, St. Louis/14617/85 clone 1A1, was isolated in primary African Green monkey kidney cells, passaged and cloned in MRC cells (1A1-MRC14), and cold-passaged 52 times in MRC-5 or Vero cells at 32 to 22° C.

A second strategy employed a biologically cloned derivative of the uncloned parental cpRSV 3131 virus. This virus was biologically cloned in bovine embryonic kidney (BEK) cells [the tissue used to originally derive the cpRSV 3131 virus—see Friedewald et al., J. Amer. Med. Assoc. 204:690–694 (1968)]. This cloned virus was then passaged at 10 day intervals in Vero cells at low temperature. Alternatively, the cpRSV 3131 virus was cloned by two serial terminal dilutions (TD2P4) in MRC-5 cells and passaged at 10-day intervals in MRC-5 or Vero cells.

The third strategy involved selection of mutants that produce large plaques at low temperature. An RSV cp3131 derivative virus designated plaque D1 that produces large plaques at 25° C. has been identified. This virus was derived from the third passage (P3) level of the cp3131-1 (BEK) lineage cp3131-17 (BEK) lineage. The largest plaque produced by P3 virus was amplified at 32° C., then re-plaqued at 25° C. Once again the largest plaque was selected, amplified, and re-plaqued. After five such cycles, large plaque mutant virus D1 was obtained. D1 was biologically cloned by two additional cycles of plaque-to-plaque purification at 25° C.

Biologically cloned virus D1 produces distinctly and uniformly larger plaques at 25° C. than cp3131 or wild type virus A2. Thus D1 is cold adapted by the criterion of large plaque size at 25° C. Efficiency of plaque formation studies demonstrated that D1 is not temperature sensitive. At 37° C., D1 plaques are indistinguishable from those of wild-type RSV or cp3131, suggesting that D1 is not restricted in growth at this temperature. Consistent with this, D1 produces extensive cytopathic effects in Vero cell monolayers at 37° C. and 40° C. (i.e. the highest temperatures tested).

EXAMPLE III

Introduction of Further Attenuating Mutations into ts-RSV

This Example describes the use of ts mutants as parental viruses to produce more completely attenuated strains. Two RSV A2 ts mutants were selected for this process, namely ts-4 and ts-1 NG1. Two distinct methods were chosen to introduce additional mutations into the RSV ts mutants. First, the incompletely attenuated RSV ts mutant was subjected to chemical mutagenesis, and mutagenized progeny that are more temperature-sensitive with regard to plaque formation were selected for further analysis. Second, the RSV ts mutants were passaged at low temperature to select RSV ts mutants with the ca phenotype, i.e., increased capacity to replicate at suboptimal temperature compared to wild-type parental virus.

A parent stock of ts-1 NG1 virus was prepared from Flow Laboratories Lot M4 of live Respiratory Syncytial Virus (A-2) ts-1 NG-1 mutant; MRC-5 grown virus. This mutant, derived from the ts-1 mutant by a second round of mutagenesis using nitrosoguanidine, possesses two or more independent ts mutations, but still induces substantial rhinorrhea in susceptible chimpanzees. This virus was passaged twice in Vero cells at 32° C. to create a ts-1 NG-1 suspension for mutagenesis. The virus was then grown in the presence of $4 \times 10^{-4}$M 5-fluorouracil to induce additional mutations during replication or was exposed to 5-azacytidine at 36° C. after 5-fluorouracil treatment. The mutagenized stock was then analyzed by plaque assay on Vero cells that were maintained under an agar overlay, and, after an appropriate interval of incubation, plaques were identified microscopically. 586 plaques were picked, and the progeny of each plaque were separately amplified by growth on fresh monolayers of Vero cells. The contents of each of the tissue cultures inoculated with the progeny of a single plaque of mutagenized ts-1 NG-1 virus were separately harvested when cytopathic effects on the Vero cells appeared maximal. Progeny virus that was more temperature-sensitive than ts-1 NG1 was sought by titering these plaque pools on HEp-2 cells at 32° C. and 36° C. Any virus exhibiting greater temperature sensitivity than ts-1 NG1 (i.e., 100-fold or greater reduction in titer at restrictive temperature [36° C.] compared to 32° C.) was evaluated further. Six plaque progeny more ts than the RSV ts-1 NG-1 parent virus were identified and these strains were biologically cloned by serial plaque-purification on Vero cells three times, then amplified on Vero cells. The cloned strains were titered at 32° C., 35° C., 36° C., 37° C., and 38° C. (efficiency of plaque formation assay) to confirm their ts phenotype. Efficiency of plaque formation data generated by assay on HEp-2 cells further confirmed the phenotype of the six mutants (Table 19).

The two most ts viruses, A-20-4 and A-37-8, where highly attenuated in mice compared to their ts-1 NG1 parent virus, indicating that acquisition of increased level of temperature sensitivity was accompanied by augmented attenuation (Table 20). These viruses were infectious for mice because they induced an antibody response. The ts-1 NG1/A-20-4 virus is attenuated for chimpanzees (Table 21) and infection of chimpanzees with ts-1 NG1/A-20-4 induced resistance to wild-type virus challenge (Table 22). Significantly, rhinorrhea does not occur.

Mutagenesis of the ts-4 virus was also performed, using the same method as for mutagenesis of ts-1 NG1, virus. Mutations were also introduced into the ts-4 viruses by cold-passage. The ts-4 virus replicates to high titer at 22° C. after 43 cold-passages. Six plaque progeny that were more ts than the RSV ts-4 parent virus were identified (Table 23). The ts-4 cp-43 is even further restricted in replication in Balb/c mice (Table 24).

TABLE 19

Efficacy of plaque formation of ts-1 NG1 derivatives

| | Titer ($log_{10}$pfu/ml) at indicated temperature | | | | |
|---|---|---|---|---|---|
| Virus | 32° | 35° | 36° | 37° | 38° |
| A-20-4(4 − 1)[a] | 5.9* | <1 | <1 | <1 | <1 |
| A-37-8(1 − 2)[a] | 6.3 | 6.3 | <1 | <1 | <1 |
| A-15-7 | 3.5 | ND | 2.1 | 1.5 | <1 |
| A-25-8 | 5.3 | ND | 5.0* | 4.8* | <1 |
| A-21 | 5.1** | ND | 4.8** | 4.5** | <1 |
| Ts1NG1 | 6.6 | 6.6 | 6.5 | 6.6 | <1 |

[a]3× plaque purified
*Small-plaque phenotype (<50% wild-type plaque size)
**Pinpoint-plaque phenotype (<10% wild-type plaque size)
ND = Not Done

TABLE 20

Replication of ts-1 NG1 parent and progeny viruses in Balb/c mice

| | Dose | Day Post- | Titer in lung | | Titer in nose | |
|---|---|---|---|---|---|---|
| Virus | ($log_{10}$pfu) | Infection | 32° | 38° | 32° | 38° |
| A2 wt | 6.1 | 4 | 4.66 ± 0.32[a] | 4.80 ± 0.16 | 3.18 ± 0.40 | 3.29 ± 0.33 |
| | | 5 | 5.18 ± 0.33 | 5.25 ± 0.23 | 3.40 ± 0.20 | 3.47 ± 0.14 |
| Ts1NG1 | 5.8 | 4 | 4.31 ± 0.17 | <2.0 | 2.82 ± 0.25 | <2.0 |
| | | 5 | 3.98 ± 0.12 | <2.0 | 2.74 ± 0.31 | <2.0 |
| Ts1NG1/A-20-4 | 6.1 | 4 | <2.0 | <2.0 | <2.0 | <2.0 |
| | | 5 | <2.0 | <2.0 | <2.0 | <2.0 |
| Ts1NG1/A-37-8 | 6.3 | 4 | <2.0 | <2.0 | <2.0 | <2.0 |
| | | 5 | <2.0 | <2.0 | <2.0 | <2.0 |

[a]Mean $log_{10}$pfu/g of indicated tissue ± standard error. 6 animals/group.

TABLE 21

Replication of ts-1 NG1/A-20-4, ts-1 NG1, ts-1 or wild-type RSV A2 in the upper and lower respiratory tract of seronegative chimpanzees.

| Animal infected with indicatel virus | Route of Inoculation[a] | Chimpanzee number | Virus replication | | | | Rhinorrhea scores | |
|---|---|---|---|---|---|---|---|---|
| | | | Nasopharypx | | Trachea | | | |
| | | | Duration[b] (Days) | Peak titer ($\log_{10}$pfu/ml) | Duration[b] (Days) | Peak titer ($\log_{10}$pfu/ml) | Mean[c] | Peak |
| ts-1NG1/A-204 | IN + IT | 15 | 0 | <0.7 | 0 | <0.7 | 0 | 0 |
| | IN + IT | 16 | 0 | <0.7 | 0 | <0.7 | 0 | 0 |
| | IN + IT | 17 | 0 | <0.7 | 0 | <0.7 | 0 | 0 |
| | IN + IT | 18 | 16[d] | 2.7 | 0 | <0.7 | 0 | 0 |
| | | | mean 4.0 | mean 1.2 | mean 0 | mean <0.7 | mean 0 | mean 0 |
| ts-1 NG1 | IN | 19[e] | 8 | 4.2 | 0 | <1.1 | 0.6 | 1 |
| | IN | 20[e] | 7 | 3.9 | 0 | <1.1 | 0.7 | 1 |
| | IN | 21[e] | 13 | 5.4 | 0 | <1.1 | 0.4 | 1 |
| | IN | 22[e] | 10 | 5.2 | 10d | 3.7d | 0.6 | 2 |
| | | | mean 9.5 | mean 4.7 | mean 2.5 | mean 1.8 | mean 0.6 | mean 1.3 |
| ts-1 | IN | 23[e] | 16 | 3.4 | 0 | <1.1 | 0.4 | 1 |
| | IN | 24[e] | 13 | 4.4 | 0 | <1.1 | 1.0 | 3 |
| | IN | 25[e] | 13 | 5.0 | 13d | 2.2 | 2.0 | 4 |
| | IN | 26[e] | 10 | 3.4 | 0 | <1.1 | 1.0 | 2 |
| | | | mean 13 | mean 4.1 | mean 3.3 | mean 1.4 | mean 1.1 | mean 2.5 |
| A2 wild-type | IN | 9[b] | 9 | 5.1 | 13 | 5.4 | 1.0 | 1 |
| | IN | 10[b] | 9 | 6.0 | 8 | 6.0 | 1.7 | 4 |
| | IN + IT | 11[e] | 13 | 5.3 | 8 | 5.9 | 2.1 | 3 |
| | IN + IT | 12[e] | 9 | 5.4 | 8 | 5.6 | 1.0 | 3 |
| | | | mean 10 | mean 5.5 | mean 9.3 | mean 5.7 | mean 1.4 | mean 2.8 |

[a]IN = Intranasal only; IN + IT = Both intranasal and intratracheal administration.
[b]Indicates last day post-infection on which virus was recovered.
[c]Mean rhinorrhea score represents the sum of daily scores for a period of eight days surrounding the peak day of virus shedding, divided by eight. Four is the highest score; zero is the lowest score.
[d]Virus isolated only on day indicated.
[e]Animals from Crowe, et al., Vaccine 11:1395–1404 (1993).

TABLE 22

Immunization of chimpanzees with $10^4$ pfu of RSV ts-1 NG1/A-204, ts-1 NG1, or ts-1 induces resistance to $10^4$ pfu RSV A2 wild-type virus challenge on day 28.

| Virus used to immunize animal | Chimpanzee number | Virus Recovery | | | | Rhinorrhea scores | | Serum neutralizing antibody titer (reciprocal $\log^2$) on day indicated[d] | |
|---|---|---|---|---|---|---|---|---|---|
| | | Nasopharynx | | Trachea | | | | | |
| | | Duration (Days) | Peak titer ($\log_{10}$pfu/ml) | Duration (Days) | Peak titer ($\log_{10}$pfu/ml) | Mean[a] | Peak | Day 28 | Day 49 or 56 |
| ts-1 NG1/A-20-4 | 15 | 0 | <0.7 | 0 | <0.7 | 0 | 0 | <3.3 | 10.7 |
| | 16 | 0 | <0.7 | 0 | <0.7 | 0 | 0 | <3.3 | 11.9 |
| | 17 | 0 | <0.7 | 0 | <0.7 | 0 | 0 | 5.3 | 10.3 |
| | 18 | 3 | 2.0 | 0 | <0.7 | 0 | 0 | 8.2 | 11.8 |
| | | mean 0.8 | mean 1.0 | mean 0 | mean <0.7 | mean 0 | mean 0 | mean 5.0 | mean 11.2 |
| ts-1 NG1 | 19[b] | 0 | <0.7 | 0 | <1.1 | 0 | 0 | 11.1 | 9.8 |
| | 20[b] | 0 | <0.7 | 0 | <1.1 | 0 | 0 | 12.7 | 9.1 |
| | 21[b] | 0 | <0.7 | 0 | <1.1 | 0 | 0 | 10.8 | 11.0 |
| | 22[b] | 0 | <0.7 | 0 | <1.1 | 0 | 0 | 10.0 | 8.6 |
| | | mean 0 | mean <0.7 | mean 0 | mean <1.1 | mean 0 | mean 0 | mean 11.1 | mesn 9.6 |
| ts-1 | 23[b] | 0 | <0.7 | 0 | <1.1 | 0 | 0 | 9.4 | 10.5 |
| | 29[b] | 0 | <0.7 | 0 | <1.1 | 0 | 0 | 12.4 | 12.8 |
| | 25[b] | 5 | 0.7 | 0 | <1.1 | 0 | 0 | 9.0 | 9.6 |
| | 26[b] | 5 | 0.7 | 0 | <1.1 | 0 | 0 | 13.4 | 12.0 |
| | | mean 2.5 | mean 0.7 | mean 0 | mean <1.1 | mean 0 | mean 0 | mean 11.0 | mean 11.2 |
| none | 9[c] | 9 | 5.1 | 13 | 5.4 | 1.0 | 1 | <3.3 | 11.0 |
| | 10[c] | 9 | 6.0 | 8 | 6.0 | 1.7 | 4 | <3.3 | 9.8 |
| | 11[b] | 13 | 5.3 | 8 | 5.9 | 2.1 | 3 | <3.3 | 9.4 |
| | 12[b] | 9 | 5.4 | 8 | 5.6 | 1.0 | 3 | <3.3 | 14.5 |
| | | mean 10 | mean 5.5 | mean 9.3 | mean 5.7 | mean 1.5 | mean2.8 | mean <3.3 | mean 11.1 |

[a]Mean rhinorrhea score represents the sum of scores during the eight days of peak virus shedding divided by eight. Four is the highest score; zero is the lowest score.
[b]Animals from Crowe, et al., Vaccine 11:1395–1404 (1993).
[c]Animals from Collins, et al., Vaccine 8:164–168 (1990).
[d]Serum neutralizing titers in this table were determined in a new assay simultaneously with other specimens represented in the table.

TABLE 23

The efficiency of plaque formation of six mutants derived from RSV ts-4 and tested in HEp-2 cells at permissive and restrictive temperatures compared with controls

| Virus | The titer of virus ($\log_{10}$pfu/ml) at the indicated temperature (°C.) | | | | | | | | | Small-plaques at 32° C. | Shut-off temperature (°C.)[1] |
|---|---|---|---|---|---|---|---|---|---|---|---|
| | 32 | 33 | 34 | 35 | 36 | 37 | 38 | 39 | 40 | | |
| A2 wild-type | 5.7 | 5.8 | 5.5 | 5.5 | 5.3 | 5.5 | 5.5 | 5.4 | 5.5 | no | >40 |
| ts-4 | 4.5 | 4.7 | 4.4 | 4.7 | 4.7 | 4.1 | 3.7 | 3.0 | 2.5 | no | 40 |
| ts-4 cp-43 | 6.2 | 6.1 | 6.1 | 6.0 | 4.4* | 4.2** | 1.7** | 0.7** | <0.7 | no | 37 |
| ts-4/20.7.1 | 6.0 | 5.9 | 5.7 | 5.7* | 4.5** | 1.8 | <0.7 | <0.7 | <0.7 | no | 37 |
| ts-4/19.1.2 | 5.8 | 5.7 | 5.5 | 5.6* | 4.4** | <0.7 | <0.7 | <0.7 | <0.7 | no | 37 |
| ts-4/15.8.2 | 5.3* | 5.4* | 4.8* | 4.9* | 2.8** | <0.7 | <0.7 | <0.7 | <0.7 | yes | 36 |
| ts-4/29.7.4 | 5.7 | 5.6 | 5.6 | 5.7* | <0.7 | <0.7 | <0.7 | <0.7 | <0.7 | no | 36 |
| ts-4/31.2.4 | 4.7 | 4.2 | 4.1 | 4.0* | <9.7 | <0.7 | <0.7 | <0.7 | <0.7 | no | 36 |

[1]Shut-off temperature is defined as the lowest restrictive temperature at which a 100-fold or greater reduction of plaque titer is observed (bold figures in table).
*Small-plaque phenotype (<50% wild-type plaque size)
**Pinpoint-plaque phenotype (<10% wild-type plaque size)

TABLE 24

Replication of RSV ts-4 and RSV ts-4 cp-43 in Balb/c mice[1]

| Virus used to infect animals: | Shutoff temperature of virus (°C.) | Virus titer (mean $\log_{10}$pfu/g tissue of six animals ± standard error) | |
|---|---|---|---|
| | | Nasal turbinates | Lungs |
| A2 wild-type | >40 | 5.0 ± 0.14 | 5.2 ± 0.05 |
| ts-4 | 39 | 4.3 ± 0.09 | 4.7 ± 0.11 |
| ts-4 cp-43 | 37 | 2.1 ± 0.09 | 2.7 ± 0.27 |

[1]Mice were administered $10^{6.3}$ p.f.u. intranasally under light anesthesia on day 0, then sacrificed by $CO_2$ asphyxiation on day 4.

Example IV

RSV Subgroup B

Vaccine Candidates

This Example describes the development of RSV subgroup B virus vaccine candidates. The same approach used for the development of the subgroup A mutants of the invention was utilized for the subgroup B viruses. A parent stock of wild-type B-1 RS virus was cold-passaged 52 times in Vero cells at low temperature (20°–25° C.) and the virus was subjected to plaque purification at passages 19 and 52. Three of the clones derived from the passage 52 suspension were evaluated independently, and one clone, designated RSV B-1cp52/2B5, was selected for further evaluation because it was highly attenuated in the upper and lower respiratory tract of the cotton rat (Table 25). An evaluation of several clones at different passage levels of the cp RSV B-1 virus indicate that the RSV B-152/2B5 mutant sustained three mutations that independently contribute to its attenuation phenotype. The RSV B-1cp52/2B5 mutant retained its attenuation phenotype following prolonged replication in immunosuppressed cotton rats (Table 26). This finding of a high level of genetic stability is consistant with the fact that it possesses three mutations contributing to the attenuation phenotype.

Further evaluation of the subgroup B mutants in order to characterize them in a similar manner as the subgroup A mutants, was carried out in Caribbean Green monkeys (Tables 27 and 28) and chimpanzees (Table 29). Monkeys immunized with either RSV B-1 cp-23 or cp-52/2B5 were resistant to replication of RSV B-1 wild-type virus, indicating that infection with the highly attenuated derivatives of the RSV B-1 wild-type virus was sufficient to induce resistance to wild-type challenge (Table 27). The results in the seronegative chimpanzee, like that in the Green monkeys, clearly evidence the attenuation of the RSV B-152/2B5 in the upper and lower respiratory tracts.

The RSV B-1cp52/2B5 mutant has been further mutagenized with 5-fluorouracil and the resulting plaques picked and screened at 32° vs. 38° C. for the ts phenotype. The selected cpts mutants were plaque-purified three times in Vero cells and then amplified twice in Vero cells. As a result, seven cpts mutants of RSV B-1cp52/2B5 have been identified (Table 30) and their level of replication in cotton rats has been studied (Table 31). One of these mutants, namely cpts176, was further mutagenized and a series of mutant derivatives were obtained that were more ts in vitro than the RSV B-1 cpts176 parent virus (Table 32).

As with the subgroup A mutants of the inventions the subgroup B mutants are infectious and exhibit a significant degree of attenuation for cotton rats, monkeys, and chimpanzees. Despite attenuation in vivo, the RSV B-1 cp mutant viruses induced resistance in monkeys against wild-type challenge. The ts mutants of the RSV B-1 cp52/2B5 virus are attenuated and demonstrate a more restricted level of replication in the nasopharynx and lungs of the cotton rat than the RSV B-1 cp52/2B5 parent virus.

TABLE 25

Replication in cotton rats of RSV B-1 wild-type compared with five plaque-purified cold-passaged mutants derived from RSV B-1, in two separate experiments

| Virus used to infect animals on day 0** | Virus recovery ($\log_{10}$pfu/g tissue) on day 4* | | | |
|---|---|---|---|---|
| | Nasal turbinates | | Lungs | |
| | Exp. 1 | Exp. 2 | Exp. 1 | Exp. 2 |
| RSV B-1 wild-type | 4.7 ± 0.14 | 5.1 ± 0.10 | 5.4 ± 0.15 | 5.8 ± 0.08 |
| RSV B-1 cp-12/B1A | nd | 3.3 ± 0.15 | nd | 4.4 ± 0.10 |

TABLE 25-continued

Replication in cotton rats of RSV B-1 wild-type compared with five plaque-purified cold-passaged mutants derived from RSV B-1, in two separate experiments

| | Virus recovery ($\log_{10}$pfu/g tissue) on day 4* | | | |
|---|---|---|---|---|
| Virus used to infect | Nasal turbinates | | Lungs | |
| animals on day 0** | Exp. 1 | Exp. 2 | Exp. 1 | Exp. 2 |
| RSV B-1 cp-23/1A1 | nd | 2.4 ± 0.36 | nd | 3.2 ± 0.31 |
| RSV B-1 cpsp-52/1A1 | 1.7 ± 0.1 | 2.1 ± 0.27 | 3.0 ± 0.13 | 2.3 ± 0.07 |
| RSV B-1 cp-52/2B5 | 1.8 ± 0.25 | 2.2 ± 0.3 | 1.8 ± 0.11 | <1.5 |
| RSV B-1 cp-52/3C1 | 1.8 ± 0.14 | nd | 1.8 ± 0.14 | nd |
| RSV A2 | 5.9 ± 0.09 | 5.4 ± 0.07 | 6.6 ± 0.06 | 6.1 ± 0.06 |
| RSV A2 cpts-530/1009 | 3.2 ± 0.1 | 2.1 ± 0.22 | 2.1 ± 0.19 | 1.7 ± 0.12 |

*Virus recovery determined by titration of tissue homogenates on Vero cell monolayer cultures at 32° C. with a 10-day incubation in Experiment 1, 7-day incubation in Experiment 2.
**Cotton rats infected intranasally with $10^{5.5}$ pfu of indicated virus.
nd = not done

TABLE 26

Growth in cotton rats of day 14 isolates* from RSV B-1 cp52/2B5-infected immunosuppressed cotton rats compared with controls

| | Virus recovery | | | |
|---|---|---|---|---|
| | Virus titer on day 4 in indicated tissue (mean $\log_{10}$pfu/g tissue ± standard error of the mean) | | Reduction of replication versus RSV B-1 wild-type ($\log_{10}$pfu/g) | |
| Virus infected animal[a] | Nasal turbinates[b] | Lungs[c] | Nasal turbinates | Lungs |
| RSV B-1 wild-type | 3.9 ± 0.03 (6/6) | 4.8 ± 0.12 (6/6) | — | — |
| RSV B-1 cp 52/2B5 | 2.0 ± 0.07 (8/8) | <1.5 (0/8) | 1.9 | >3.3 |
| isolate 1 | 1.5 ± 0.13 (5/8) | 1.5 ± 0.04 (1/8) | 2.5 | 3.3 |
| isolate 2 | 1.5 ± 0.13 (6/8) | <1.5 (0.8) | 2.4 | >3.3 |
| isolate 3 | 1.5 ± 0.16 (3/8) | <1.5 (0/8) | 2.5 | >3.3 |
| isolate 4 | 1.3 ± 0.09 (4/8) | <1.5 (0/8) | 2.6 | >3.3 |
| isolate 5 | 1.2 ± 0.00 (2/8) | <1.5 (0/8) | 2.7 | >3.3 |
| isolate 6 | 1.2 ± 0.00 (3/8) | <1.5 (018) | 2.7 | >3.3 |
| isolate 7 | 1.3 ± 0.06 (3/8) | <1.5 (0/8) | 2.7 | >3.3 |

*Isolates were virus suspensions obtained following amplification by one Vero cell tissue culture passage of virus present in the original nasal turbinate homogenate on day 14 of an immunosuppressed cotton rat.
[a]Groups of 8 cotton rats infected with $10^{5.5}$ pfu of indicated virus in a 0.1 ml inoculum on day 0.
[b]() indicates the numbers of animals from which virus was detected at 1.2 $\log_{10}$ pfu/g or greater.
[c]() indicates the numbers of animals from which virus was detected at 1.5 $\log_{10}$pfu/g or greater.

TABLE 27

Replication in Caribbean Green monkeys of RSV A2 and RSV B-1 wild-types compared with that of two cold-passaged mutants derived from RSV B-1, followed by homologous or heterologous RSV A2 or B-1 wild-type challenge

| | Immunization | | | | | Challenge | |
|---|---|---|---|---|---|---|---|
| | NP swab | | Tracheal lavage | | | NP swab | Tracheal lavage |
| Virus used to infect animals on day 0[a] | Peak titer[b] | Days shed[b] | Peak titer | Days shed | Challenge virus | Peak titer[b] | Peak titer[b] |
| A2 | 3.4 | 9 | <0.7 | 0 | A2 | <0.7 | <0.7 |
| | 3.5 | 7 | <0.7 | 0 | A2 | <0.7 | <0.7 |
| | 3.5 | 9 | 4.8 | 10 | A2 | <0.7 | <0.7 |
| | 3.2 | 8 | 0.7 | 7 | A2 | <0.7 | <0.7 |
| | 1.7 | 6 | <0.7 | 0 | B-1 | <0.7 | <0.7 |
| | 3.5 | 10 | <0.7 | 0 | B-1 | <0.7 | <0.7 |
| | 2.4 | 8 | 0.7 | 0 | B-1 | <0.7 | <0.7 |
| | 4.2 | 9 | <0.7 | 0 | B-1 | <0.7 | <0.7 |
| | mean 3.2 | mean 8.3 | mean 1.2 | | | | |
| B-1 | 2.8 | 9 | 1.5 | 10* | B-1 | <0.7 | <0.7 |
| | 2.3 | 9 | 1.9 | 7 | B-1 | <0.7 | <0.7 |
| | 2.2 | 7 | 1.7 | 10* | B-1 | <0.7 | <0.7 |
| | 2.2 | 9 | 1.3 | 10* | B-1 | <0.7 | <0.7 |
| | 1.6 | 8* | 1.2 | 5* | A2 | <0.7 | <0.7 |
| | 2.1 | 10 | 1.7 | 7* | A2 | <0.7 | <0.7 |
| | mean 2.2 | mean 8.7 | mean 1.6 | | | mean <0.7 | mean <0.7 |
| B-1 cp-23 | 1.8 | 14 | <0.7 | 0 | B-1 | <0.7 | <0.7 |
| | 1.3 | 5 | <0.7 | 0 | B-1 | <0.7 | <0.7 |
| | 2.0 | 8 | 0.7 | 10 | B-1 | <0.7 | <0.7 |
| | 1.7 | 4 | <0.7 | 0 | B-1 | <0.7 | <0.7 |
| | mean 1.7 | mean 7.8 | mean <0.7 | | | mean <0.7 | mean <0.7 |
| B-1 cp-52 | 1.3 | 8 | <0.7 | 0 | B-1 | <0.7 | <0.7 |
| | 1.3 | 4 | <0.7 | 0 | B-1 | <0.7 | <0.7 |
| | 1.3 | 7 | <0.7 | 0 | B-1 | <0.7 | <0.7 |

TABLE 27-continued

Replication in Caribbean Green monkeys of RSV A2 and RSV B-1 wild-types compared with that of two cold-passaged mutants derived from RSV B-1, followed by homologous or heterologous RSV A2 or B-1 wild-type challenge

| | Immunization | | | | | Challenge | |
|---|---|---|---|---|---|---|---|
| | NP swab | | Tracheal lavage | | | NP swab | Tracheal lavage |
| Virus used to infect animals on day 0[a] | Peak titer[b] | Days shed[b] | Peak titer | Days shed | Challenge virus | Peak titer[b] | Peak titer[b] |
| | 0.7 | 3 | <0.7 | 0 | B-1 | <0.7 | <0.7 |
| | mean 12 | mean 5.5 | mean <0.7 | | | mean <0.7 | mean <0.7 |

[a]Animals infected intratracheally and intranasally with $10^{5.5}$ p.f.u. virus at each site in a 1.0 ml inoculum on day 0.
[b]$\text{Log}_{10}$pfu/ml titers determined by plaque assay on HEp-2 cell monolayer cultures for RSV A2, and Vero cell monolayer cultures for RSV B-1 and its derivatives.
*Virus detected only on day indicated

TABLE 28

Neutralizing antibody response of Caribbean Green Monkeys infected with RSV A2, RSV B-1, or B4 cp derivatives, then challenged with homologous or heterologous wild-type virus one month later.

| Animals infected on day 0 with indicated virus (number of animals) | Day 28 challenge virus (number of animals) | 60% Plaque reduction serum neutralizing titer against indicated virus (reciprocal mean) | | | | | |
|---|---|---|---|---|---|---|---|
| | | RSV A2 | | | RSVB-1 | | |
| | | Day 0 | Post-infection (day 28) | Post-challenge (day 56) | Day 0 | Post-infection (day 28) | Post-challenge (day 56) |
| A2 (8) | A2 (4) | <10 | 53,232 | 40,342 | <10 | 1,552 | 1,911 |
| | B-1 (4) | | | 23,170 | | | 1,911 |
| B4 (6) | B-1 (4) | <10 | 3,327 | 3,822 | <10 | 2,048 | 2,521 |
| | A2 (2) | | | 30,574 | | | 35,120 |
| B-1 cp-23 (4) | B-1 (4) | <10 | 6,208 | 10,086 | <10 | 4,705 | 7,132 |
| B-1 cp-52/2B5 (4) | B-1 (4) | <10 | 194 | 16,384 | <10 | 239 | 3,822 |

Antigenic relatedness of RSV A2 and RSV B-1 by cross-neutralization in Green Monkeys, calculated using Archetti-Korsfall formula = 47%

$$R = 100 \times \frac{\text{(heterologous 2)}}{\text{(homologous 1)}} \times \frac{\text{(heterologous 1)}}{\text{(homologous 2)}}$$

TABLE 29

The replication of RSV B-1 or RSV B-1 cp-52 in seronegative chimpanzees following simultaneous intratracheal and intranasal administration.

| Animal infected with indicated virus on day 0 | Infection dose (pfu) | Exp. | Virus replication | | | | Rhinorrbea score | |
|---|---|---|---|---|---|---|---|---|
| | | | Nasopharynx | | Trachea | | | |
| | | | Duration[b] (days) | Peak titer ($\log_{10}$pfu/ml) | Duration[b] (days) | Peak titer ($\log_{10}$pfu/ml) | Peak | Mean[c] |
| RSV B-1 wild-type | $10^4$ | 1 | 9 | 3.7 | 8 | 3.2 | 1 | 0.5 |
| | | 1 | 10 | 3.5 | 0 | <0.7 | 2 | 0.9 |
| | | 1 | 10 | 2.8 | 0 | <0.7 | 3 | 1.1 |
| | | 1 | 10 | 2.7 | 8 | 3.4 | 3 | 0.9 |
| | | | avg. 9.8 | mean 3.2 | avg. 4.0 | mean 2.0 | mean 23 | mean 0.9 |
| | $10^5$ | 2 | 7 | 2.8 | 8 | 1.0 | 1 | 1.0 |
| | | 2 | 7 | 3.3 | 4 | 3.9 | 3 | 1.3 |
| | | | avg. 7.5 | mean 3.1 | avg. 6.0 | mean 2.5 | mean 2.0 | meart 1.1 |

TABLE 29-continued

The replication of RSV B-1 or RSV B-1 cp-52 in seronegative chimpanzees following simultaneous intratracheal and intranasal administration.

| Animal infected with indicated virus on day 0 | Infection dose (pfu) | Exp. | Virus replication | | | | Rhinorrbea score | |
|---|---|---|---|---|---|---|---|---|
| | | | Nasopharynx | | Trachea | | | |
| | | | Duration[b] (days) | Peak titer ($log_{10}$pfu/ml) | Duration[b] (days) | Peak titer ($log_{10}$pfu/ml) | Peak | Mean[c] |
| B-1 cp-52/2B5 | $10^4$ | 1 | 5 | 1.5 | 0 | <0.7 | 0 | 0 |
| | | 1 | 0 | <0.7 | 0 | <0.7 | 0 | 0 |
| | $10^5$ | 3 | 0 | <0.7 | 0 | <0.7 | 0 | 0 |
| | | 3 | 0 | <0.7 | 0 | <0.7 | 0 | 0 |
| | | | avg. 1.2 | mean 0.9 | avg. 0 | mean <0.7 | mean 0 | mean 0 |

[a]These data were combined from three separate experiments, the infection dose of indicated virus in the first experiment was $10^4$, the second and third experiments were $10^5$.
[b]Indicates the last day post-infection on which virus was recovered.
[c]Mean rhinorrhea score represents the sum of daily scores for a period of eight days surrounding the peak day of virus shedding, divided by eight Four is the highest score; zero is the lowest score.

TABLE 30

The efficiency of plaque formation of eight mutants derived from RSV B-1 cp52/2B5
Plaque titer ($log_{10}$pfu/ml in Vero of HEp-2 Cells at indicated temperatures (°C.)

| RSV | Vero | HEp-2 | | | | | | HEp-2 Shutoff temp (°C.) |
|---|---|---|---|---|---|---|---|---|
| | 32 | 32 | 35 | 36 | 37 | 38 | 39 | |
| B-1 wild-type | 6.1 | 5.8 | 5.7 | 5.6 | 5.6 | 5.7 | 5.5 | >39 |
| B-1 cp-52/2B5 | 5.9 | 5.4 | 5.2 | 5.1 | 5.0 | 5.0 | 4.7** | 39 |
| cpts-452 | 6.1 | 5.6 | 5.2 | 5.2 | 3.3** | 3.1** | <0.7 | 37 |
| cpts-1229 | 5.7 | 5.1 | 4.9 | 5.1 | 4.4** | <0.7 | <0.7 | 38 |
| cpts-1091 | 5.7 | 5.1* | 4.7** | 5.2** | <0.7 | <0.7 | <0.7 | 37 |
| cpts-784 | 5.1 | 4.3* | 4.0** | 4.1** | <0.7 | <0.7 | <0.7 | 37 |
| cpts-176 | 6.1 | 5.4* | 4.8** | 5.0** | <0.7 | <0.7 | <0.7 | 37 |
| cptssp-1415[a] | 5.8 | <0.7 | <0.7 | <0.7 | <0.7 | <0.7 | <0.7 | 38 |
| cpts-1324 | 5.9 | 5.1 | 5.0* | 5.0 | <0.7 | <0.7 | <0.7 | 37 |
| cpts-1313 | 5.7 | 3.9** | 3.0** | <0.7 | <0.7 | <0.7 | <0.7 | 36 |
| A2 | 6.4 | 6.3 | 6.3 | 6.3 | 6.3 | 6.3 | 6.3 | >39 |
| A2/248 | 6.3 | 6.3 | 6.2 | 6.3 | 5.8 | <0.7 | <0.7 | 38 |
| A2/248/404 | 4.4 | 4.3 | 3.3 | 4.0 | <0.7 | <0.7 | <0.7 | 37 |
| A2/248/955 | 4.8 | 4.8 | 4.8 | 4.4 | <0.7 | <0.7 | <0.7 | 37 |

*Small-plaque phenotype (<50% wild-type plaque size).
**Pinpoint-plaque phenotype (<10% wild-type plaque size).
Bold figures denote shutoff temperatures (defined as the lowest restrictive temperature at which a 100-fold or greater reduction of plaque fiter was observed).
[a]At 32° C., no plaques were observed. Therefore, no shut-off temperature was determined by efficiency of plaque formation. The mutant was assigned a shutoff temperature of 38° C. in HBp-2 cell culture as determined by a 100-fold decrease in virus yield ($TCID_{50}$) in liquid medium overlay.

TABLE 31

Level of replication in cotton rats of seven ts mutants derived from RSV B-1 cp-52/2B5

| RSV | Replication in cotton rats[1] (mean $log_{10}$pfu/g tissue of six animals ± s.e.) | | | |
|---|---|---|---|---|
| | Nasal turbinates | | Lungs | |
| B-1 wild-type | 4.3 ± 0.05 | (6/6)[2] | 4.4 ± 0.25 | (6/6) |
| B-1 cp-52/2B5 | 1.7 ± 0.11 | (6/6) | <1.5 | (0/6) |
| cpts-452 | 1.4 ± 0.1 | (3/6) | <1.5 | (0/6) |
| cpts-1091 | 1.7 ± 0.07 | (4/6) | <1.5 | (0/6) |
| cpts-784 | 1.5 | (1/6) | <1.5 | (0/6) |
| cpts-1229 | 1.4 ± 0.15 | (3/6) | <1.5 | (0/6) |
| cpts-176 | 1.5 ± 0.17 | (3/6) | <1.5 | (0/6) |
| cptssp-1415 | <1.2 | (0/6) | <1.5 | (0/6) |
| cpts-1324 | <1.2 | (0/6) | <1.5 | (0/6) |

[1]Cotton rats were inoculated intranasally with 4.5–5.8 $log_{10}$pfu under light anesthesia on day 0, then sacrificed by $CO_2$ asphyxiationon day 4.
[2]Titer from samples containing virus only. Parentheses indicate fraction of samples containing virus.

TABLE 32

The efficiency of plaque formation of 14 mutants derived from RSV
B-1 cpts-176, compared with controls
In vitro efficiency of plaque formation in HEp-2 cell monolayer culture

| RSV | The titer of virus ($\log_{10}$pfu/ml) at the indicated temperature (°C.) | | | | Shut-off temperature (°C)[1] |
|---|---|---|---|---|---|
| | 32 | 35 | 36 | 37 | |
| B-1 wild-type | 5.6 | 5.5 | 5.4 | 5.3 | >39 |
| B-1 cp-52/2B5 | 5.7 | 5.7 | 5.6 | 5.3 | >39 |
| B-1 cpts176 | 5.5 | 3.5 | 3.0 | 1.9 | 36/37 |
| 176/645 | 3.8 | 3.0 | 2.6 | <0.7** | 37 |
| 176/860 | 3.1 | 2.5 | 2.4 | <0.7 | 37 |
| 176/196 | 3.3 | 2.5 | 2.0 | <0.7** | 37 |
| 176/219 | 2.6 | 2.3 | 2.0 | <0.7** | 37 |
| 176/18 | 4.0 | 3.2 | <0.7 | <0.7 | 36 |
| 176/73 | 2.6 | 2.0 | <0.7 | <0.7 | 36 |
| 176/1072 | 3.2 | 2.3 | <0.7 | <0.7 | 36 |
| 176/1038 | 2.8 | 2.2 | <0.7 | <0.7 | 36 |
| 176/81 | 2.2 | 2.0 | <0.7 | <0.7 | 36 |
| 176/1040 | 3.2 | 2.0 | <0.7 | <0.7 | 36 |
| 176/1045 | 2.5 | 1.9 | <0.7 | <0.7 | 36 |
| 176/517 | 3.1 | 2.0 | <0.7** | <0.7 | 36 |
| 176/273 | 2.3 | <0.7 | <0.7 | <0.7 | 35 |
| 176/427 | 3.5 | <0.7 | <0.7 | <0.7 | 35 |

**Pinpoint-plaque phenotype (<10% wild-type plaque size)
[1]Shut-off temperature is defined as the lowest restrictive temperature at which a 100-fold or greater reduction of plaque titer is observed (bold figures in table).

Example V

Bivalent RSV Subgroup A and B Vaccine

Studies with subgroup A and B viruses demonstrate that in vitro, no interference occurs between wild-type A2 and B-1 viruses, nor between cpts RSV 530/1009 and RSV B-1 cp-52/2B5 derivatives in Vero cell monolayer cultures. The in vivo results of bivalent infection in cotton rats are presented in Table 33. These results confirm the in vitro results, which show no interference between A-2 and B-1 wild-type RSV, and cpts RSV 530/1009 and RSV B-1 cp-52/2B5. It is expected, therefore, that each vaccine virus will induce homotypic immunity against wild-type virus, since each component of the bivalent vaccine replicates to a level in the dual infection comparable to that seen during single infection. Each virus alone is capable of inducing homotypic resistance against RSV wild-type challenge.

TABLE 33

Bivalent infection of cotton rats with RSV A2 and RSV B-1 viruses or mutant derivatives indicates no in vivo interference

| Viruses used to infect animals* | Virus recovery from indicated tissue ($\log_{10}$pfu/g) | | | |
|---|---|---|---|---|
| | Nasal turbinates | | Lungs | |
| | RSV A titer | RSV B titer | RSV A titer | RSV B titer |
| A2 | 5.4 ± 0.08 | — | 5.8 ± 0.07 | — |
| B-1 | — | 4.6 ± 0.03 | — | 5.4 ± 0.12 |
| A2 + B-1 | 5.2 ± 0.11 | 3.6 ± 0.07 | 5.7 ± 0.08 | 5.0 ± 0.05 |
| A2cpts-530/1009 | 3.2 ± 0.09 | — | 1.9 ± 0.15 | — |
| B-1 cp-52 | — | 2.4 ± 0.08 | — | <1.5 |
| A2 cpts-530/1009 + B1 cp-52 | 2.8 ± 0.13 | 2.0 ± 0.14 | 1.8 ± 0.08 | <1.5 |

*Groups of six animals infected with $10^5$ pfu intranasally on day 0 in a 0.1 ml inoculum.

Human Studies

The attenuated virus of the invention is administered to human subjects according to well established human RS vaccine protocols, as described in, e.g., Wright et al., *Infect. Immun.* 37:397–400 (1982), Kim et al., *Pediatrics* 52:56–63 (1973), and Wright et al., *J. Pediatr.* 88:931–936 (1976), which are incorporated herein by reference. Briefly, adults or children are inoculated intranasally via droplet with $10^3$ to $10^6$ PFU of attenuated virus per ml in a volume of 0.5 ml. Antibody response is evaluated by complement fixation, plaque neutralization, and/or enzyme-linked immunosorbent assay. Individuals are monitored for signs and symptoms of upper respiratory illness. As with administration to chimpanzees, the attenuated virus of the vaccine grows in the nasopharynx of vaccinees at levels approximately 10-fold or more lower than wild-type virus, and approximately 10-fold or more lower when compared to levels of cpRSV or other incompletely attenuated parental strain. Subsequent immunizations are administered periodically to the individuals as necessary to maintain sufficient levels of protective immunity.

From the foregoing it will be appreciated that, although specific embodiments of the invention have been described herein for purposes of illustration and understanding, various modifications may be made without deviating from the spirit and scope of the invention. Accordingly, the invention is not limited except as by the appended claims.

What is claimed is:

1. An immunogenic composition comprising, in a physiologically acceptable carrier, at least one attenuated respiratory syncytial virus having at least two attenuating mutations, which is a temperature sensitive respiratory syncytial virus mutant having further temperature sensitive mutations.

2. The immunogenic composition according to claim 1, which induces a respiratory syncytial virus specific immune response in seropositive individuals having a titer of RSV neutralizing antibody of at least 1:20.

3. The immunogenic composition according to claim 2, wherein the seropositive individuals having a titer of RSV neutralizing antibody of at least 1:20 are infants possessing transplacentally acquired RSV neutralizing antibodies.

4. The immunogenic composition according to claim 1, which further comprises an adjuvant to enhance the immune response.

5. The immunogenic composition of claim 1, wherein the attenuated virus is at least one selected from subgroup A and subgroup B.

6. The immunogenic composition of claim 1, wherein the attenuated virus is of a strain of subgroup A.

7. The immunogenic composition of claim 1, wherein the attenuated virus is of a strain of subgroup B.

8. The immunogenic composition of claim 1, formulated in a dose of $10^3$ to $10^6$ PFU of attenuated virus.

9. A method for stimulating respiratory syncytial virus specific immune response, which comprises administering to an individual an immunologically sufficient amount of at least one attenuated virus which is a temperature sensitive respiratory syncytial virus having further temperature sensitive mutations in a physiologically acceptable carrier.

10. The method of claim 9, wherein the attenuated virus is administered to the individual in a amount of $10^3$ to $10^6$ PFU.

11. The method of claim 9, wherein the attenuated virus is administered to the upper respiratory tract of said individual.

12. The method of claim 9, wherein the attenuated virus is administered to the nasopharynx.

13. The method of claim 11, wherein the attenuated virus is administered by spray, droplet, or aerosol.

14. The method of claim 9, wherein the attenuated virus is administered to a seronegative individual having a titer of RSV neutralizing antibodies of less than 1:20.

15. The method of claim 9, wherein the attenuated virus is administered to a seropositive individual having a titer of RSV neutralizing antibodies of at least 1:20.

16. The immunogenic composition according to claim 1, which induces a respiratory syncytial virus specific immune response in a seronegative individual having a titer of RSV neutralizing antibody of less than 1:20.

* * * * *